(12) United States Patent  (10) Patent No.: US 10,016,222 B2
Cronen  (45) Date of Patent: Jul. 10, 2018

(54) CIRCUMFERENTIAL VERTEBRAL COLUMN FIXATION SYSTEM

(71) Applicant: Geoffrey Cronen, Tampa, FL (US)

(72) Inventor: Geoffrey Cronen, Tampa, FL (US)

( * ) Notice: Subject to any disclaimer, the term of this patent is extended or adjusted under 35 U.S.C. 154(b) by 0 days.

(21) Appl. No.: 14/829,157

(22) Filed: Aug. 18, 2015

(65) Prior Publication Data

US 2016/0051284 A1 Feb. 25, 2016

Related U.S. Application Data

(60) Provisional application No. 62/038,917, filed on Aug. 19, 2014.

(51) Int. Cl.
*A61B 17/70* (2006.01)
*A61B 17/17* (2006.01)
*A61B 17/86* (2006.01)

(52) U.S. Cl.
CPC ...... *A61B 17/7032* (2013.01); *A61B 17/1757* (2013.01); *A61B 17/7001* (2013.01); *A61B 17/8625* (2013.01); *A61B 2017/7073* (2013.01)

(58) Field of Classification Search
CPC .. A61B 17/70–17/7061; A61B 17/80–17/8095
USPC ................................. 606/250–253
See application file for complete search history.

(56) References Cited

U.S. PATENT DOCUMENTS

| | | | | |
|---|---|---|---|---|
| 3,659,595 A * | 5/1972 | Haboush | ............ | A61B 17/8009 606/71 |
| 5,085,660 A * | 2/1992 | Lin | ................... | A61B 17/8057 606/288 |
| 5,591,235 A | 1/1997 | Kuslich | | |
| 6,113,600 A * | 9/2000 | Drummond | ........ | A61B 17/7049 606/250 |
| 6,355,038 B1 | 3/2002 | Pisharodi | | |
| 6,471,704 B2 | 10/2002 | Gertzbein et al. | | |
| 6,706,045 B2 | 3/2004 | Lin et al. | | |
| 2007/0123881 A1 * | 5/2007 | Ralph | ................ | A61B 17/8023 606/281 |
| 2007/0129719 A1 * | 6/2007 | Kendale | ............ | A61B 1/00096 606/41 |
| 2009/0228046 A1 * | 9/2009 | Garamszegi | ....... | A61B 17/7052 606/278 |
| 2010/0305616 A1 | 12/2010 | Carbone | | |
| 2012/0265203 A1 * | 10/2012 | Angelucci | .......... | A61B 17/7059 606/70 |

(Continued)

OTHER PUBLICATIONS

International Search Report and Written Opinion, issued by the Korean Intellectual Property Office dated Nov. 18, 2015 for PCT/US2015/045698, 12 pages.

*Primary Examiner* — Nicholas Plionis
(74) *Attorney, Agent, or Firm* — Perkins Coie LLP

(57) ABSTRACT

A circumferential vertebral column fixation systems includes an elongated engagement bar including at least two spaced apart fastener holes configured to be positioned within a vertebral body or other spinal bony segment such that fasteners inserted into the vertebral body or spinal bony segment are provided with an anchor point to help prevent fastener pull out. The engagement bar can further include a locking bar disposed within the engagement bar which can lock the fasteners to the engagement bar. Methods of using the circumferential vertebral column fixation system are also disclosed.

6 Claims, 41 Drawing Sheets

(56) References Cited

U.S. PATENT DOCUMENTS

2013/0023994 A1\* 1/2013 Glerum .................. A61F 2/447
623/17.16

\* cited by examiner

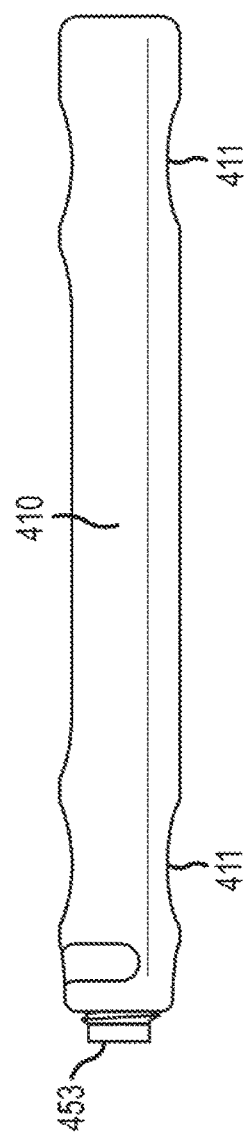
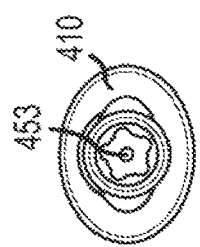
FIG.4D
FIG.4C

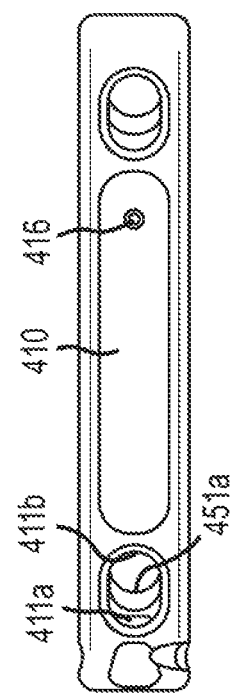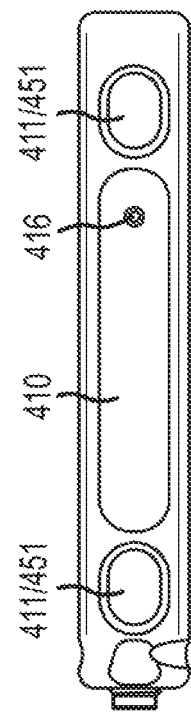

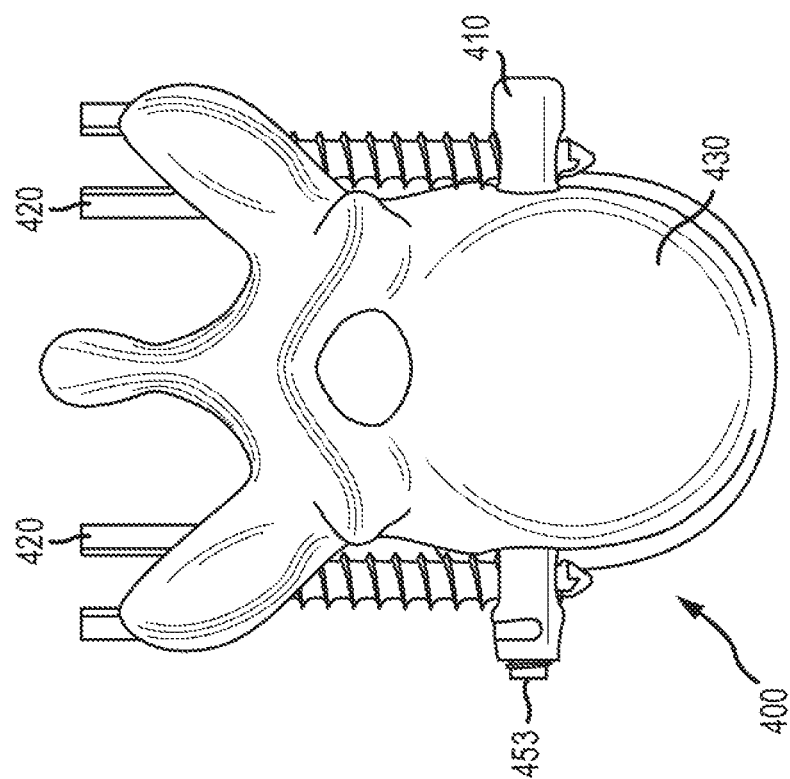
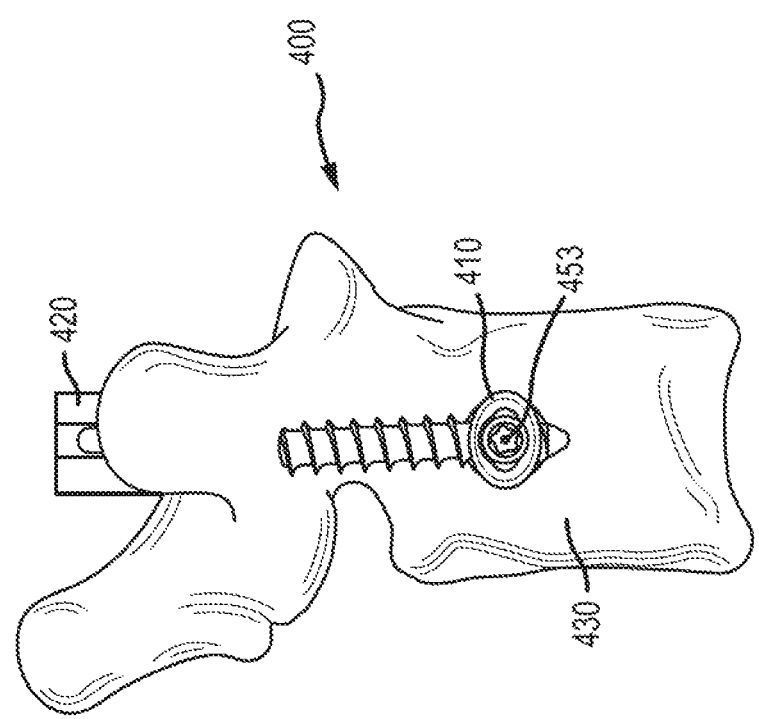

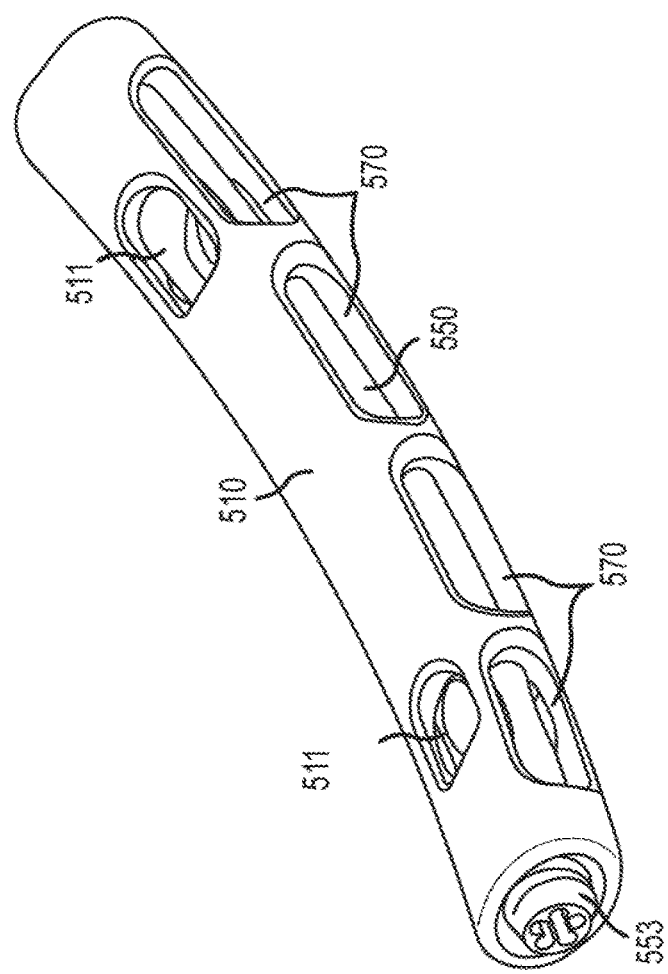
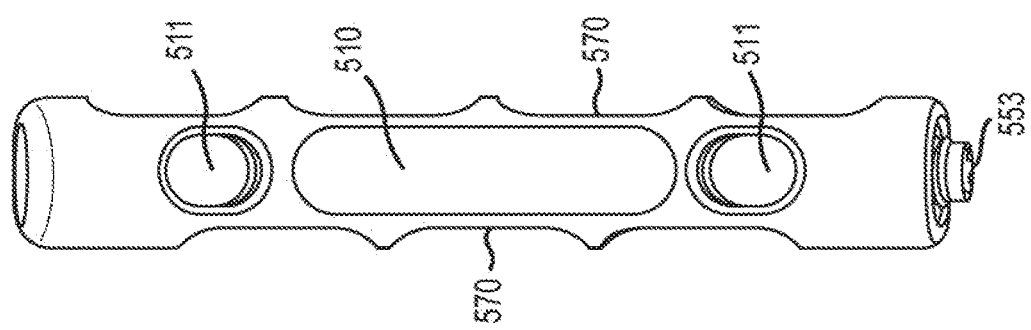
FIG. 5B
FIG. 5A

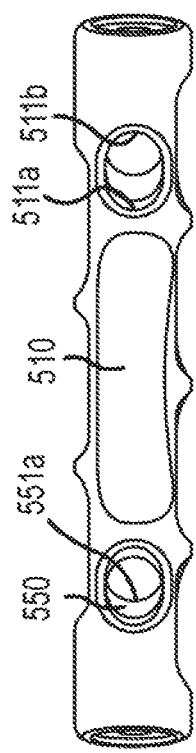
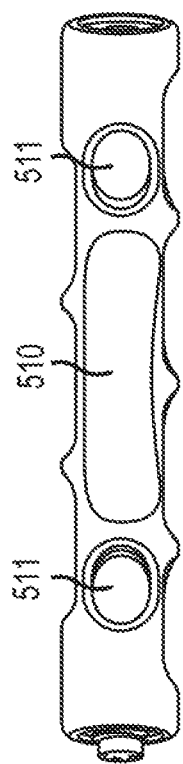
FIG.5F
FIG.5G

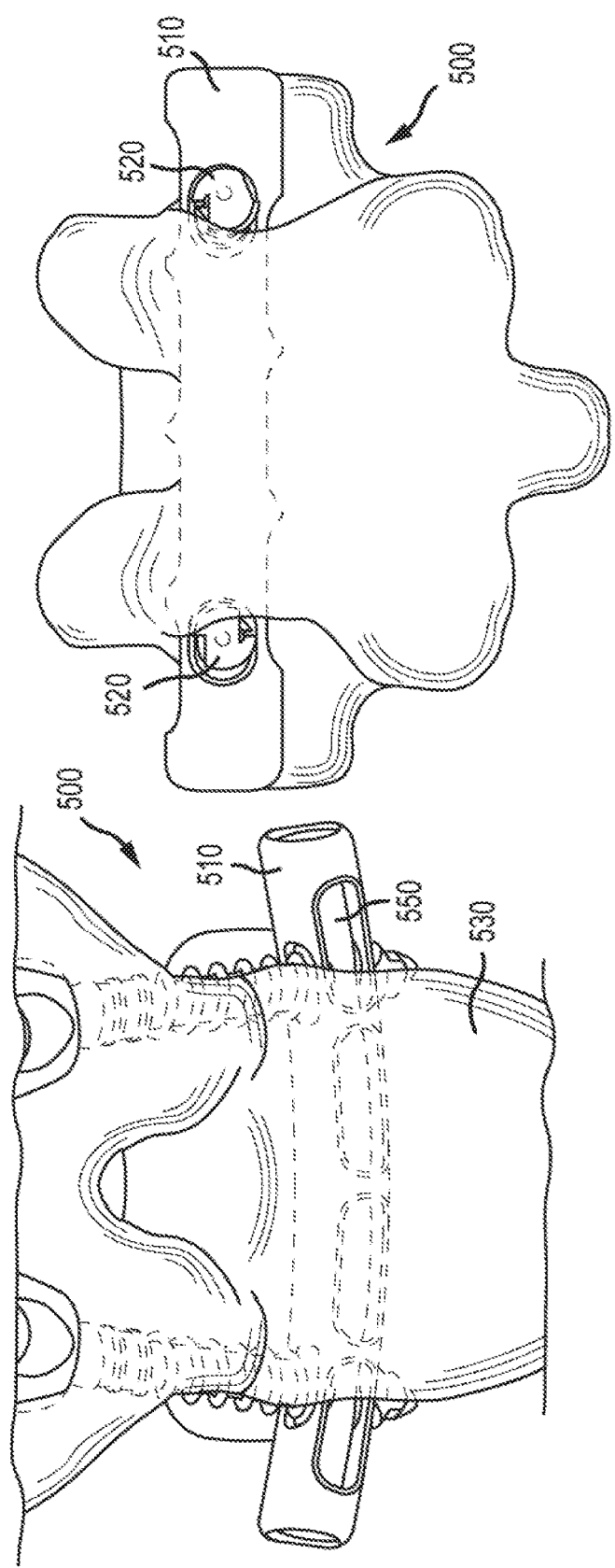

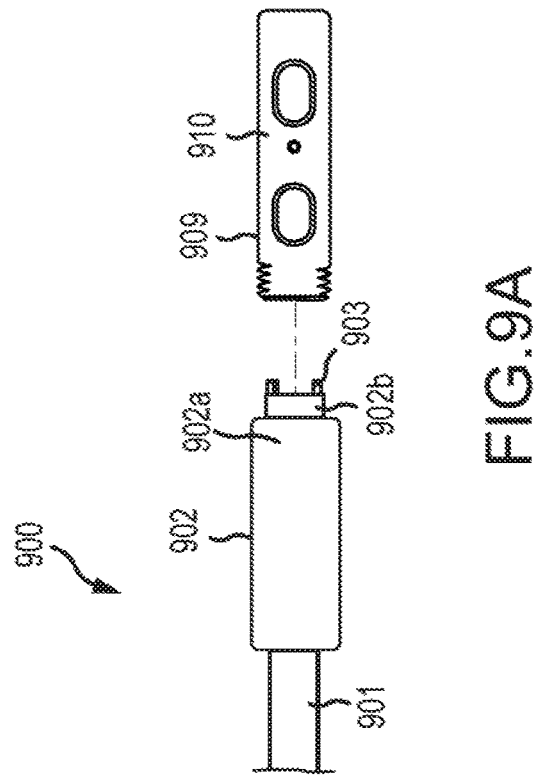
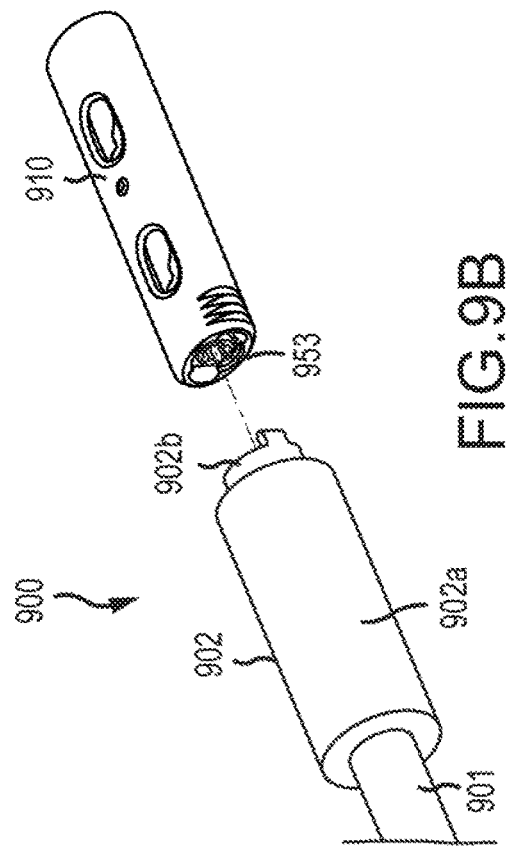

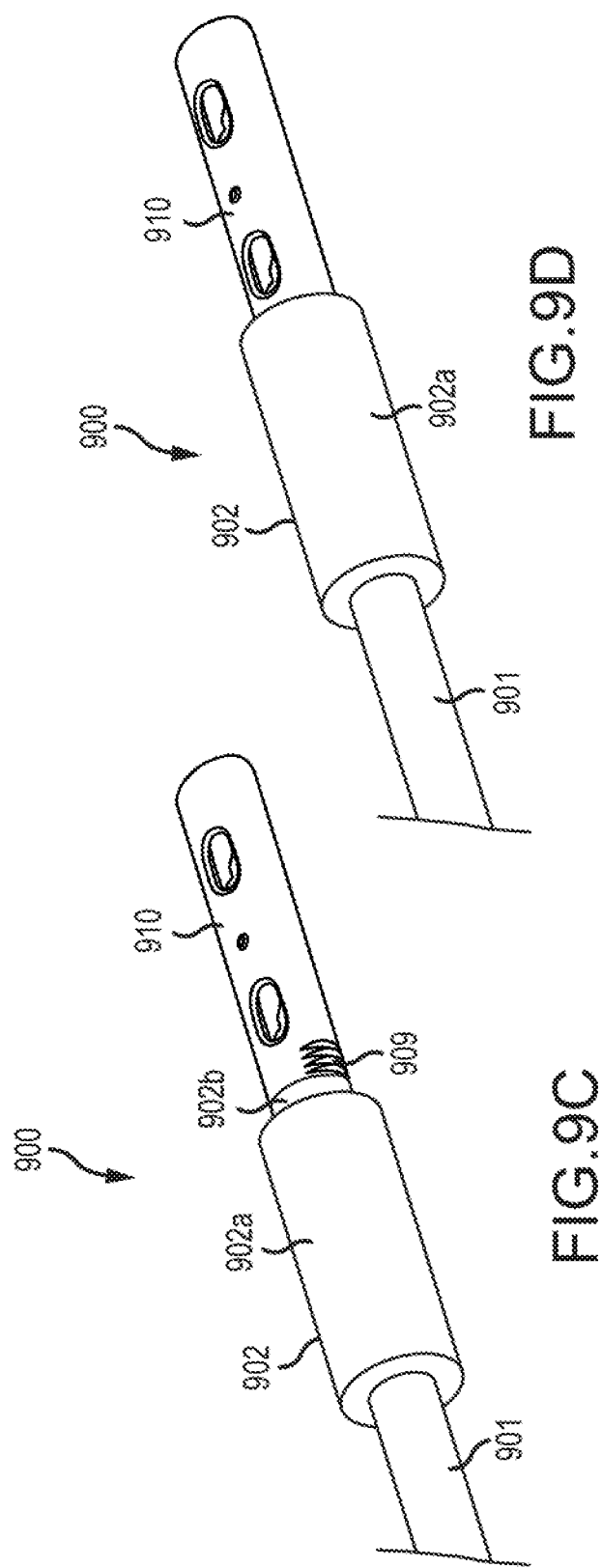

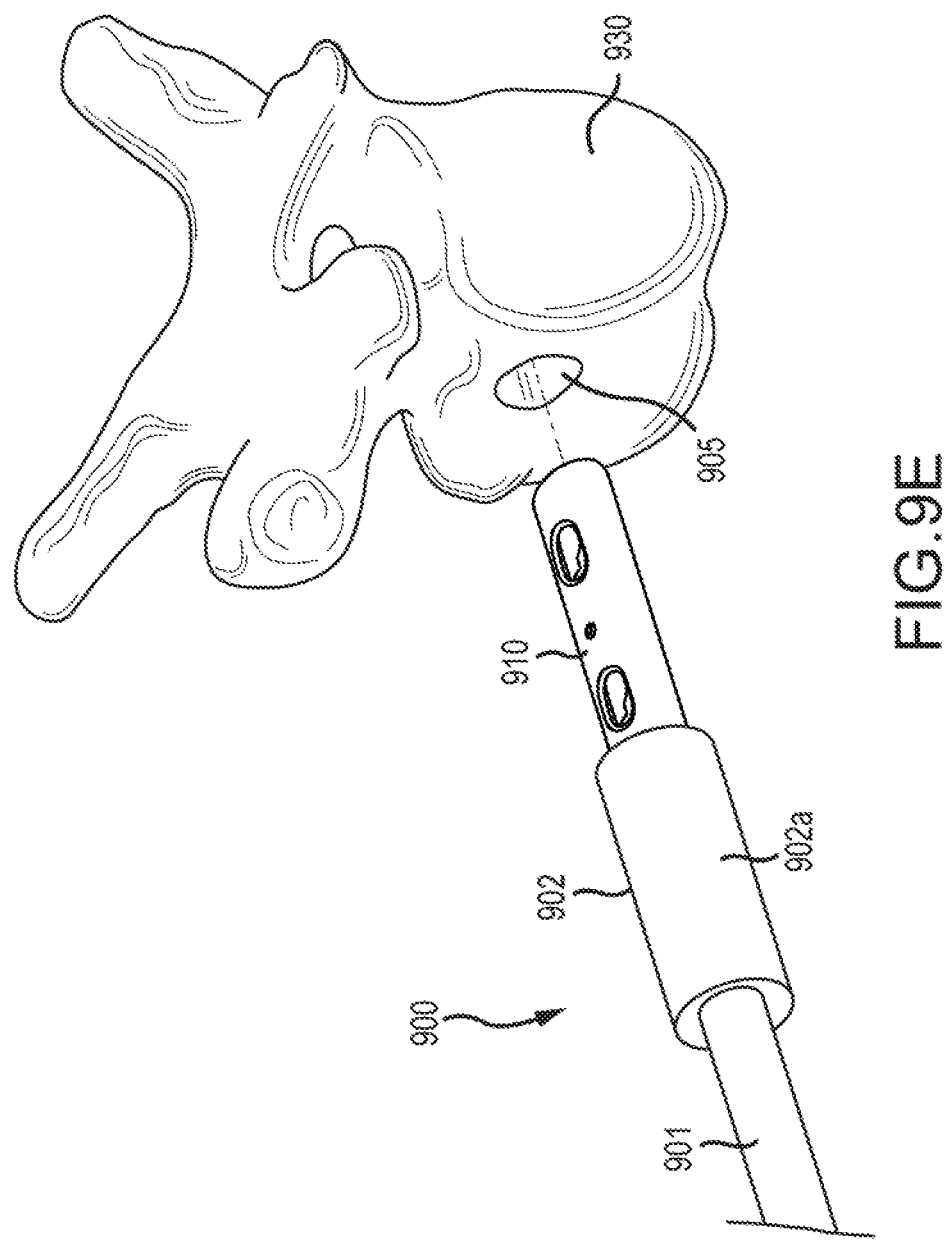

CIRCUMFERENTIAL VERTEBRAL COLUMN FIXATION SYSTEM

CROSS-REFERENCE TO RELATED APPLICATION(S)

This application claims priority to U.S. Provisional Application No. 62/038,917, filed Aug. 19, 2014, the entirety of which is hereby incorporated by reference.

BACKGROUND

In severe spinal deformity, complex revision spine surgery, and patients with compromised bone stock, bone screw fixation to vertebral bodies can be problematic and less than optimal. Screw pullout and lack of fixation points can limit the surgeon's ability to safely and adequately complete fixation.

Current and past vertebral fixation devices generally depend on uni- or bilateral fixation of bone screws to vertebral bodies. The bone screws are generally inserted into vertebral bodies, but have no anchor point within the vertebral body, and therefore can suffer from screw pullout.

SUMMARY

Disclosed herein are various embodiments of circumferential vertebral column fixation systems, methods of using the same, and insertion tools suitable for use with the disclosed circumferential vertebral column fixation systems. In some embodiments, the system includes an elongated engagement bar including at least two spaced apart fastener holes. The fastener holes each include a first opening in a top surface of the engagement bar and a second opening in the bottom surface of the engagement bar opposite the top surface. In some embodiments, the axes of the at least two fastener holes are also generally aligned in parallel. The system can further include at least two fasteners configured to engage with the at least two fastener holes of the elongated engagement bar.

In some embodiments, elongated engagement bar further includes a hollow passage having an opening at one end of the elongated engagement bar, and the system further includes an elongated locking bar configured to fit within the hollow passage and move back and forth along the longitudinal axis of the hollow passage. The locking bar can include at least two spaced apart locking holes, with the axes of the at least two locking holes being generally aligned in parallel. In some embodiments, the at least two locking holes are spaced apart a similar distance to the at least two fastener holes in the elongated engagement bar.

In some embodiments, a method of surgically installing a circumferential vertebral fixation system in a patient in need thereof is disclosed. The method can include the steps of forming a passage through a vertebral body in a transcorporeal direction; inserting an elongated engagement bar in the passage, the elongated engagement bar comprising at least two spaced apart fastener holes, wherein the axes of the at least two fastener holes are generally aligned in parallel and wherein the elongated engagement bar is positioned in the passage such that the fastener holes are aligned in a antero-posterio direction; and inserting a fastener through at least a portion of each pedicle, into the vertebral body, and into each of the two fastener holes of the elongated engagement bar.

In some embodiments, a method of surgically installing a circumferential vertebral fixation system in a patient in need thereof, includes the steps of forming a passage through a vertebral body in a trans-corporeal direction; inserting an elongated engagement bar having a locking bar disposed therein; inserting a fastener through at least a portion of each pedicle, into the vertebral body, and into each of the two fastener holes of the elongated engagement bar and each of the two locking holes of the elongated locking bar; and moving the elongated locking bar through the hollow passage in a direction towards a leading end of the elongated engagement bar to thereby pin the fastener between a leading end of the fastener hole and a trailing end of the locking hole.

BRIEF DESCRIPTION OF THE DRAWINGS

FIGS. 4A-4M illustrate various views of a circumferential vertebral column fixation system in accordance with various embodiments described herein, including views of the circumferential vertebral column fixation system implanted in a vertebra.

FIGS. 5A-5M illustrate various views of a circumferential vertebral column fixation system in accordance with various embodiments described herein, including views of the circumferential vertebral column fixation system implanted in a vertebra.

FIGS. 9A-9E illustrate various views of an insertion tool suitable for use with a circumferential vertebral column fixation system according to various embodiments described herein.

DETAILED DESCRIPTION

In the description provided below, reference is generally made to the use of the disclosed circumferential vertebral column fixation system in connection with a vertebra or vertebral body. However, discussion of vertebra or a vertebral body in the description below should be considered merely representative of any spinal bony segment with which the disclosed system can be used. In other words, it is contemplated that the systems and methods described herein can be used in connection with a vertebra or vertebral body as well as any other spinal bony segment. For example, the systems described herein can be used in the ilium or sacrum in a similar manner as described with respect to use of the system in a vertebra or vertebral body.

With reference to FIGS. 1A-1H, an embodiment of a circumferential vertebral column fixation system 100 is shown. The system 100 generally includes an elongated engagement bar 110 (as shown in, for example, FIGS. 1A-1D) and one or more fasteners 120 (as shown in, for example, FIGS. 1E-1H). As discussed further below, the fasteners 120 are generally configured to engage with the engagement bar 110 in order to serves an anchor point that helps to prevent the fasteners 120 from fastener pull out.

The elongated engagement bar 110 generally has a length L that is longer than the width W or height H in order to form the generally elongate shape. As shown in, for example, FIG. 1B, the engagement bar 110 can have a generally square or rectangular cross-section, though more circular or oval cross-sections are also possible.

Figure 1B:
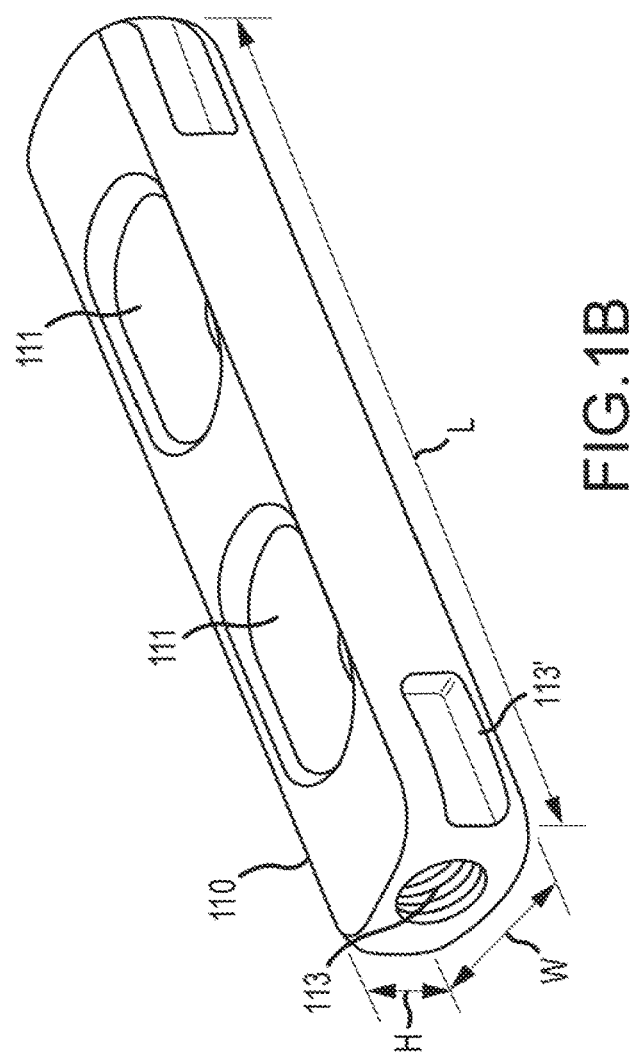
FIGS. 1A-1H illustrate various views of a circumferential vertebral column fixation system in accordance with various embodiments described herein, including views of the circumferential vertebral column fixation system implanted in a vertebra.
Figure 1A:
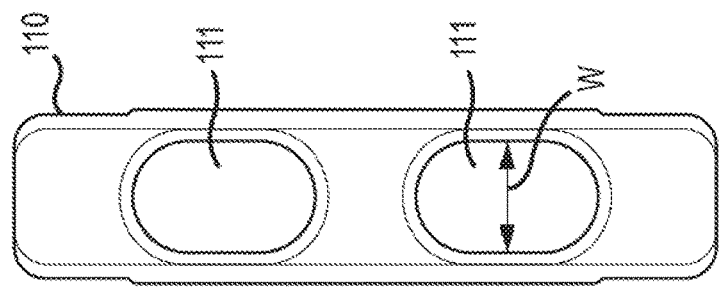
Figure 1D:
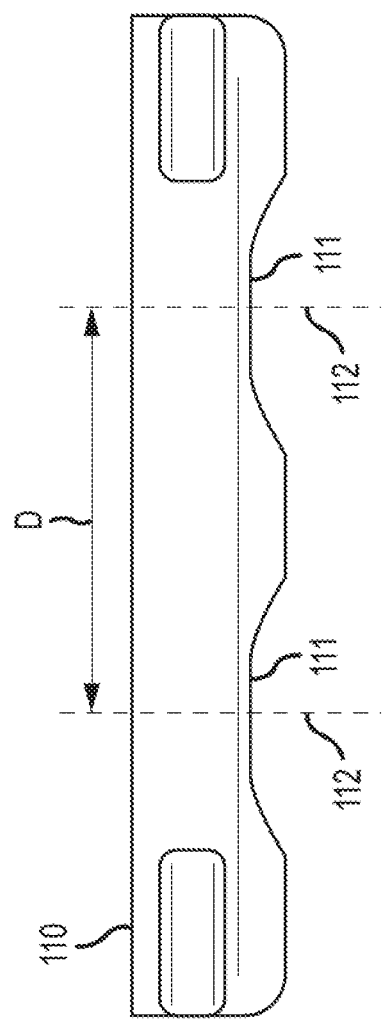
Figure 1C:
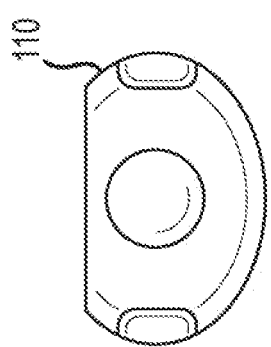

The elongated engagement bar 110 generally includes at least one engagement hole 111 configured to receive a fastener 120. FIGS. 1A and 1B show the elongated engagement bar 110 having two engagement holes 111, though fewer or more engagement holes 111 are possible. As shown in FIGS. 1A and 1B, the engagement holes 111 pass all the way through the engagement bar 110, though in alternative embodiments, one or more of the engagement holes need not pass all the way through the engagement bar 110. When the engagement bar 110 includes more than one engagement hole 111, the engagement holes 111 are generally spaced apart a distance D as shown in FIG. 1D. Notice, the engagement holes 111 may be pre-formed in the engagement bar 110 or may be drilled into the engagement bar 110 by a surgeon prior to implantation.

As shown most clearly in FIG. 1D, each engagement hole 111 includes a central axis 112. In some embodiments, the engagement holes 111 are aligned such that the central axes 112 of the engagement holes 111 are generally parallel to one another. The central axes 112 need not be perfectly parallel, and some minor angulation is possible. Generally speaking, the axes 112 should be approximately parallel as a means to ensure that the top openings of each engagement hole 111 are on the same face of engagement bar 110 and the bottom openings of each engagement hole 111 are on the same face of the engagement bar 110 (which will generally be opposite the face of the top openings of engagement holes 111). For example, as shown in FIGS. 1A-1H, the engagement bar 110 generally includes a top planar surface and a bottom planar surface opposite the top planar surface. In some embodiments, the top opening of each engagement hole 111 is in the top surface of the engagement bar 110, and the bottom opening of each engagement hole 111 is in the bottom surface of the engagement bar 110.

In some embodiments, the engagement holes 111 are shaped such that the width w of the engagement hole 111 in at least one direction is approximately equal to the diameter of the fastener 120 to be inserted therein. This helps to provide a friction fit between the engagement hole 111 and the fastener 120 that establishes the desired anchor effect between the fastener 120 and the engagement bar 110. As shown in, for example, FIGS. 1A and 1B, the side walls of the engagement holes 111 are smooth. However, in alternate embodiments, the side walls of the engagement holes 111 can be textured, such as with one or more ridges, in order to provide a more secure friction fit between the fastener 110 and the engagement hole 111. As shown in, for example, FIGS. 1G and 1H, the fastener 120 can have texturing along its body (e.g., threading), which further helps to establish the friction fit. In embodiments where the fastener 120 includes threading, the side walls of the engagement holes 111 can include threading adapted to mate with the threading of the fastener 120 to establish a secure connection between the fastener 120 and the engagement bar 110. As shown in, for example, FIGS. 1A and 1B, the engagement holes 111 may be elongated in the length L direction to facilitate placement of fasteners 120 within the engagement holes 111.

Figure 1F:
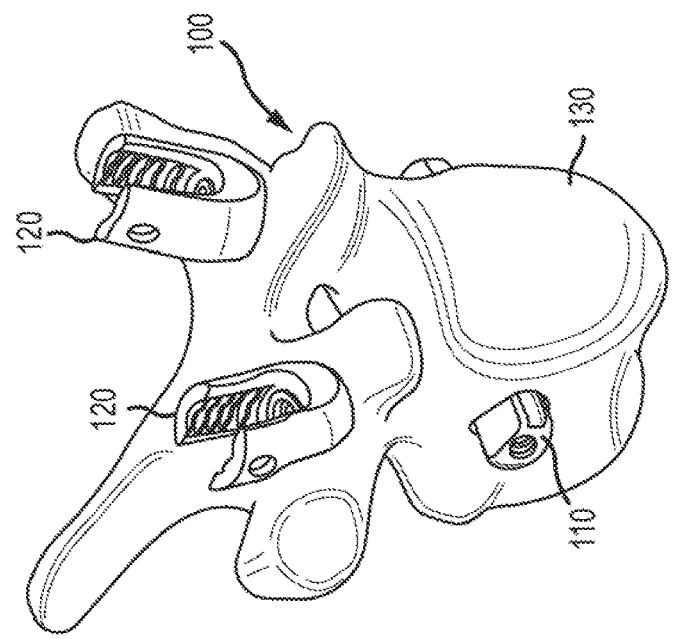
Figure 1E:
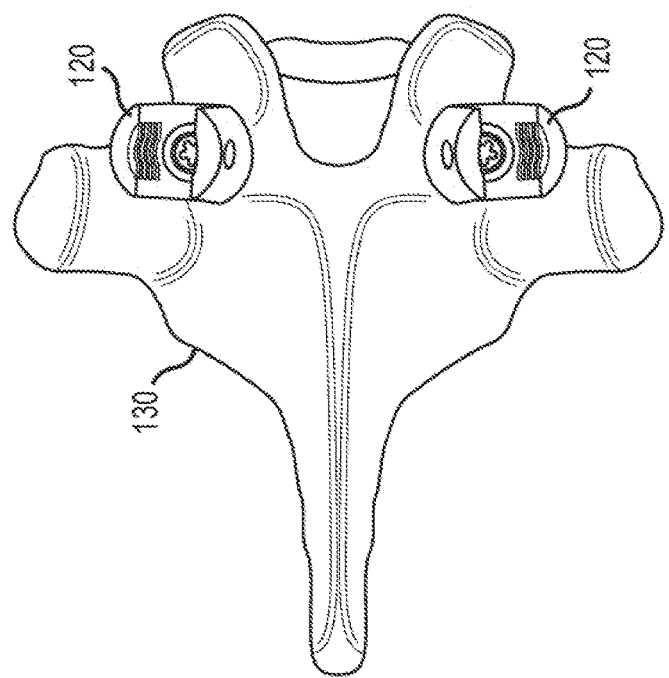
Figure 1H:
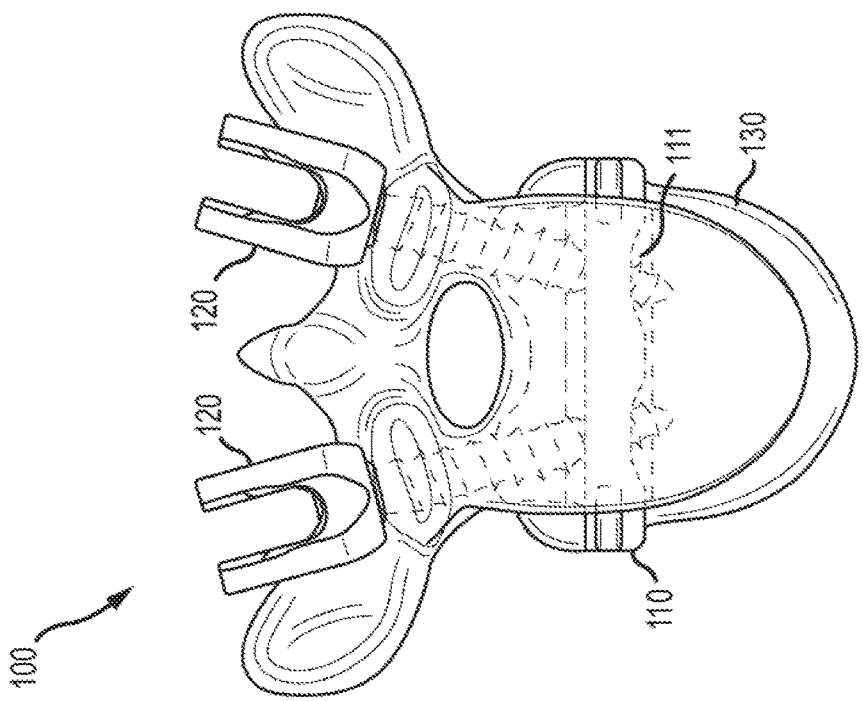
Figure 1G:
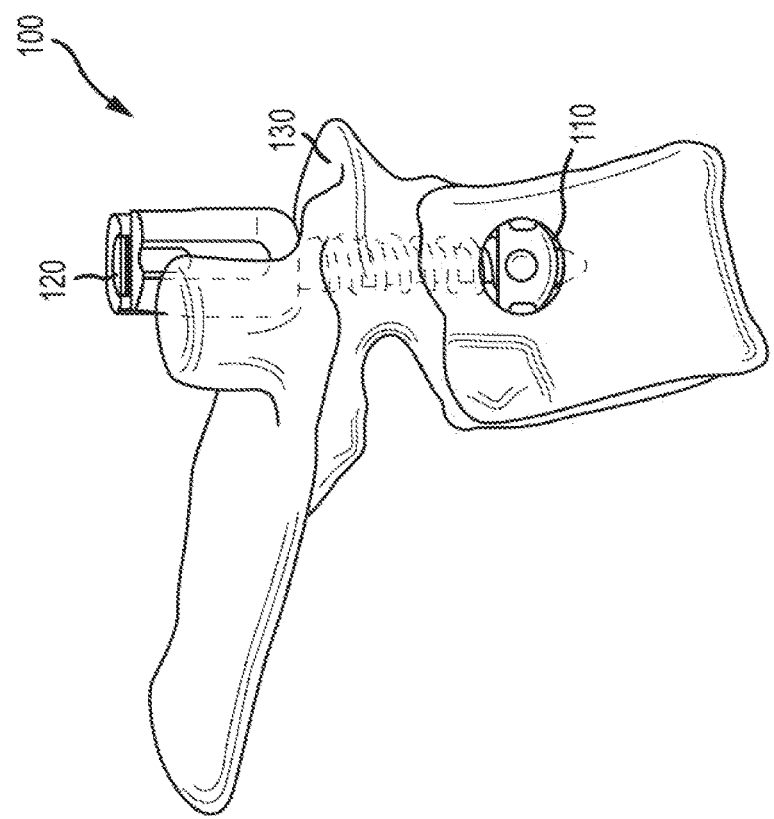

With reference now to FIGS. 1E-1G, the system 100 is shown surgically implanted in a vertebra 130 of a patient. The engagement bar 110 is inserted in a trans-corporeal passage drilled or otherwise formed into the vertebral body. Any suitable manner of forming this passage in the vertebral body can be used. As most clearly shown in FIG. 1H, the engagement bar 110 is positioned in the passage such that the engagement holes 111 face in an antero-posterio direction. After placement of the engagement bar 110 in the passage, fasteners 120 are inserted into the vertebra through the pedicles. As the fasteners 120 move into the vertebral body, they pass into and engage with one of the engagement holes 111. As discussed above, the engagement can be a friction fit due to the similar sizes of the fastener 120 and the engagement hole 111 and/or due to additional texturing included on either or both of the engagement hole 111 and the fastener 120.

Any type of fastener 120 suitable for use in surgical procedures involving vertebra can be used in the system 100. As shown in FIGS. 1E-1H, the fasteners 120 are pedicles screws having tulip heads. The tulip heads of the pedicles screws can be used to receive rods used in various spine correction surgeries.

Referring back to FIG. 1B, it can be seen that the engagement bar 110 can include a threaded hole 113 at one end of the elongated engagement bar 110. The threaded hole 113 can be used with an insertion tool in order to assist in the placement of the engagement bar 110 in the passage formed in the vertebra 130. In some embodiments, the insertion tool includes a threaded end that mates with the threaded hole 113 to provide a surgeon with the ability to both guide the engagement bar 110 into the passage and rotate the engagement bar 110 into the correct position (i.e., such that the engagement holes 111 are facing in an anterio-posterio direction) via the insertion tool. Once the engagement bar 110 is positioned in the passage and appropriately rotated, the surgeon can unscrew the insertion tool from the engagement bar 110 and separate the insertion tool from the engagement bar 110. Rather than or in combination with threaded hole 113, the engagement bar 110 may include divots 113'. The divots 113' would allow for an insertion/removal tool to grip or clamp the engagement bar 110.

With reference now to FIGS. 2A-2H, another embodiment of the circumferential vertebral body fixation system is illustrated. The system 200 shown in FIGS. 2A-2H is similar to the system 100 shown in FIGS. 1A-1H, but the engagement bar 210 includes a lower profile intermediate section 240. The lower profile intermediate section 240 generally has a length L' less than length L of the overall engagement bar 210. As shown in FIGS. 2A-2H, the length L' of the lower profile intermediate section 240 can extend a majority of the length L of the engagement bar 210, though shorter or longer lengths L' are also possible. As also shown in FIG. 2A-2H, the engagement holes 211 can be located within the lower profile intermediate section 240.

Figure 2B:
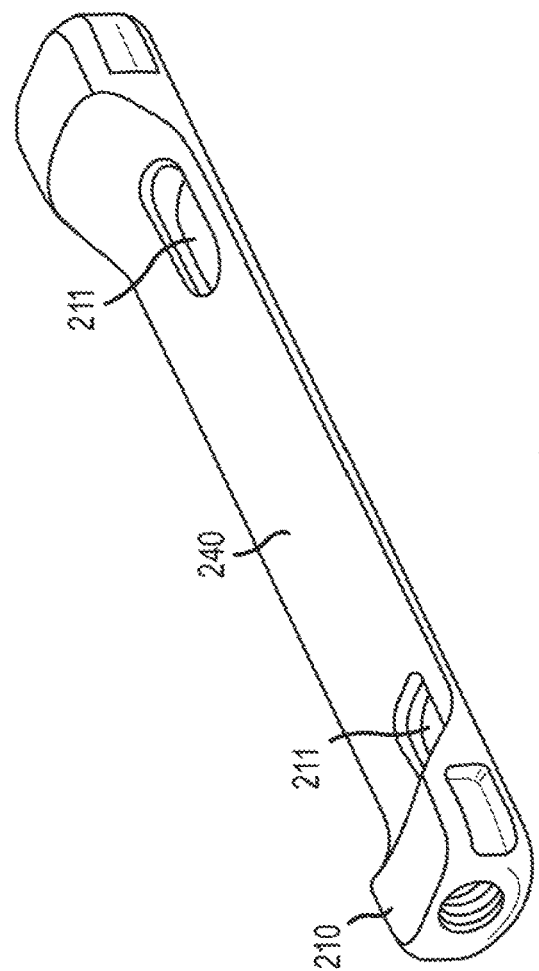
FIGS. 2A-2H illustrate various views of a circumferential vertebral column fixation system in accordance with various embodiments described herein, including views of the circumferential vertebral column fixation system implanted in a vertebra.
Figure 2A:
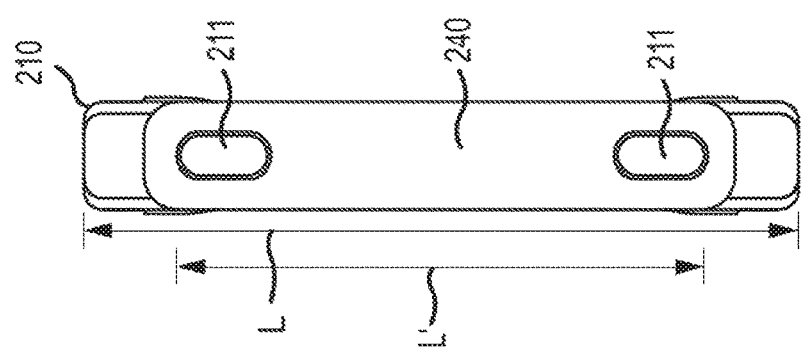
Figure 2D:
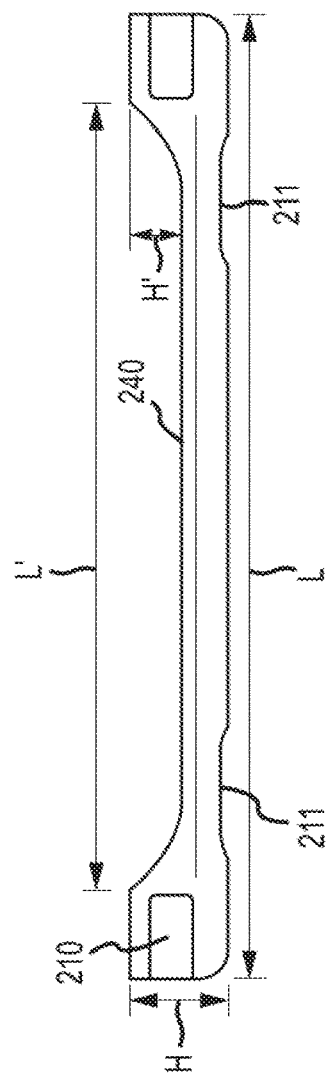
Figure 2C:
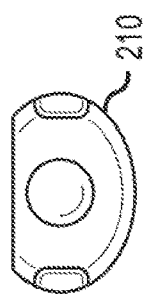

As most clearly shown in FIG. 2D, the lower profile intermediate section 240 generally has a height H' that is smaller than the overall height H of the engagement bar 240. In FIG. 2D, height H' is only slightly smaller than height H such that the portion of the engagement bar 210 below the lower profile intermediate section 240 is relatively thin. Any difference between height H' and height H can be used, including a relatively large difference, in which case the portion of the engagement bar 210 below the lower profile intermediate section 240 will be relatively thick.

Figure 2F:
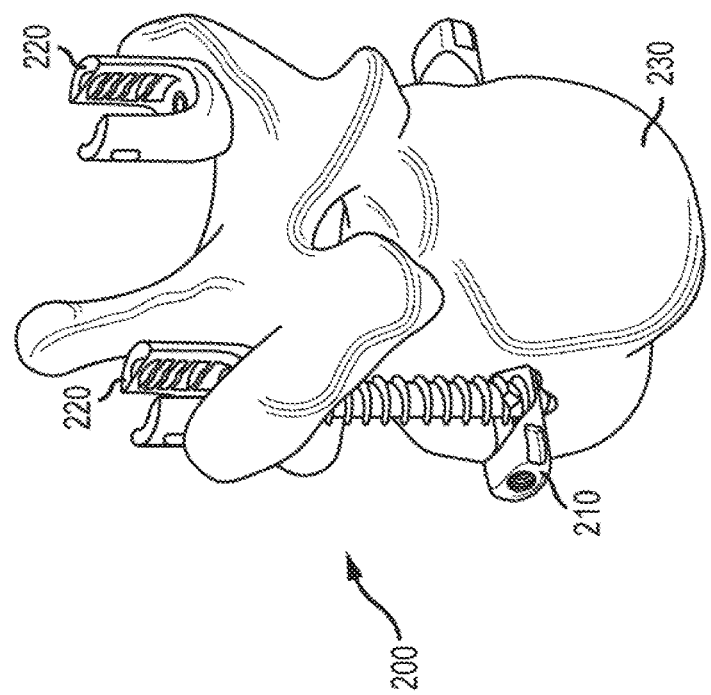
Figure 2E:
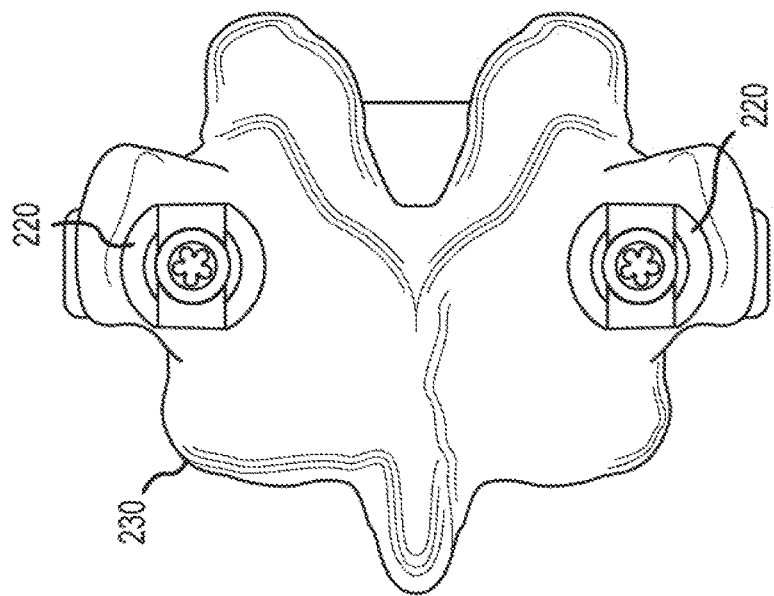
Figure 2H:
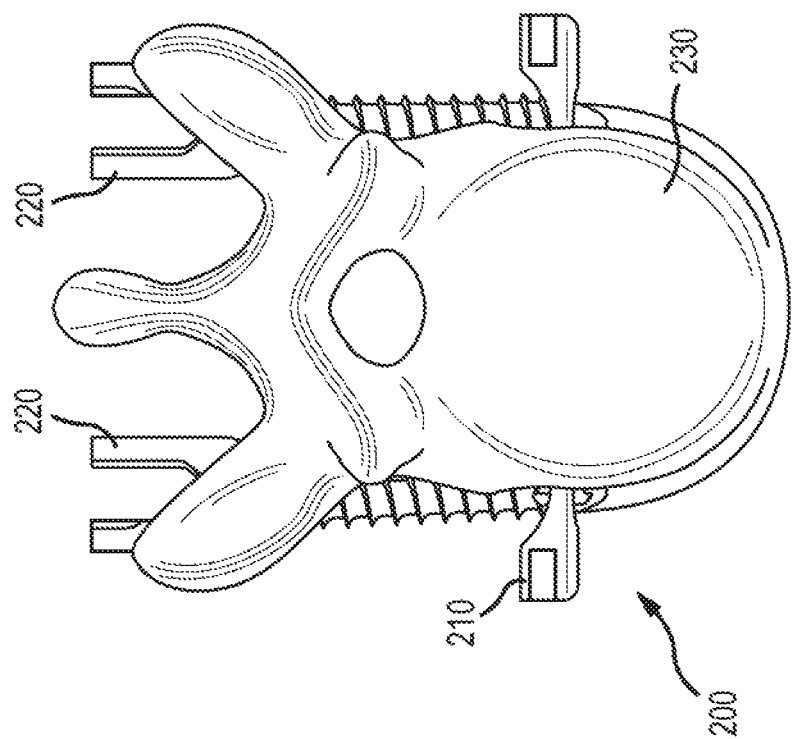
Figure 2G:
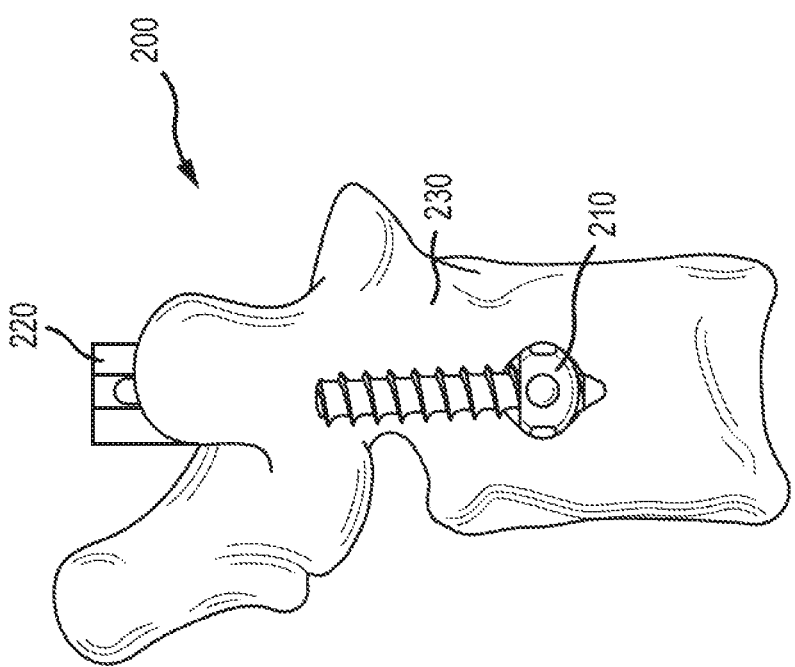

FIGS. 2E-2H show the system 200 implanted in a vertebra 230 in a similar manner as described above with respect to system 100 and FIGS. 1E-1H. FIGS. 2F and 2H show how fasteners 220 engaged with engagement holes 211 in engagement 210 may not and need not be fully (or even partially) embedded within the vertebral body. As shown in, for example, FIG. 2F, the leading end of the fastener 220 engages with the engagement bar 210 almost completely outside of the vertebral body. This embodiment illustrates how the system described herein can be useful for providing an engagement point for a fastener when one may not be available within the vertebral body. Rather than threading 314, the threading may be barbs to resist pull out of the engagement bar 310.

With reference to FIGS. 3A-3H, another embodiment of a the circumferential vertebral body fixation system is illustrated. The system 300 shown in FIGS. 3A-3H is similar to the systems 100, 200 shown in FIGS. 1A-1H and 2A-2H, but the engagement bar 310 includes external threading 314 and pointed end 315 to assist with the implantation of the engagement bar 310 into the vertebral body 330.

Figure 3B:
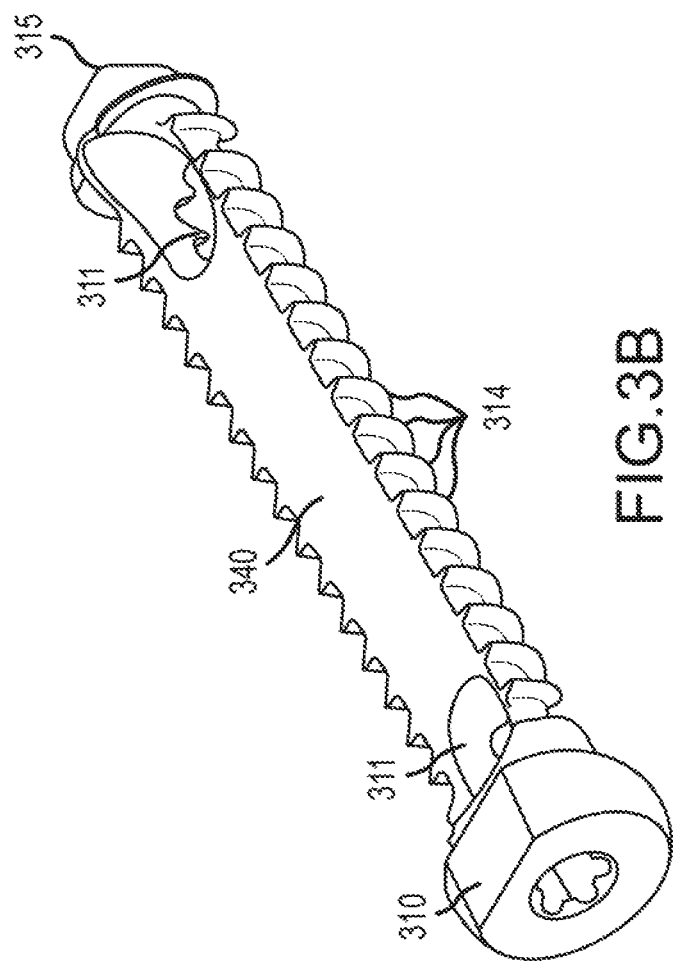
FIGS. 3A-3H illustrate various views of a circumferential vertebral column fixation system in accordance with various embodiments described herein, including views of the circumferential vertebral column fixation system implanted in a vertebra.
Figure 3A:
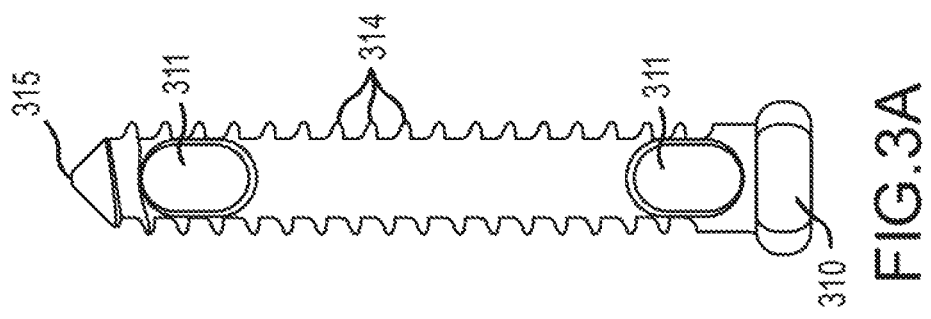
Figure 3D:
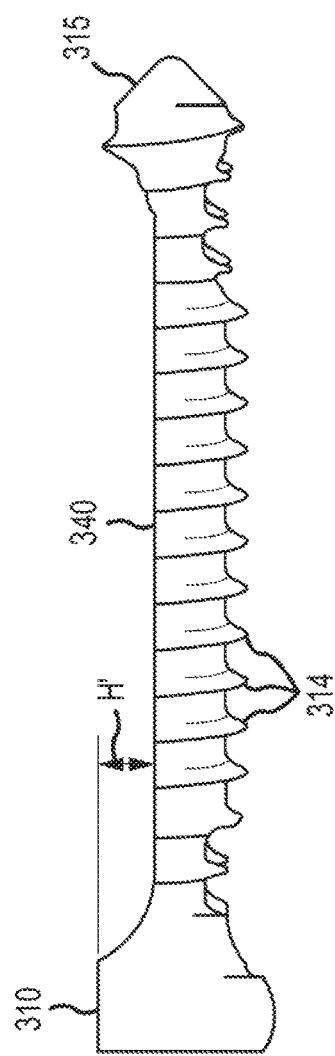
Figure 3C:
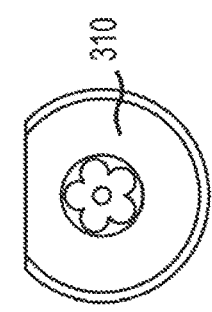
Figure 3F:
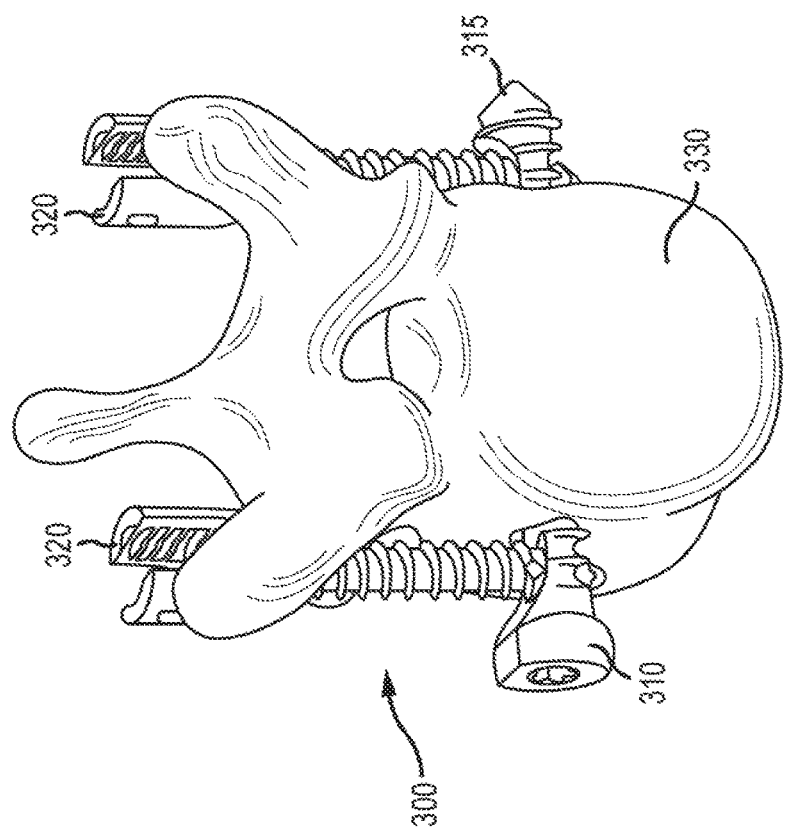
Figure 3E:
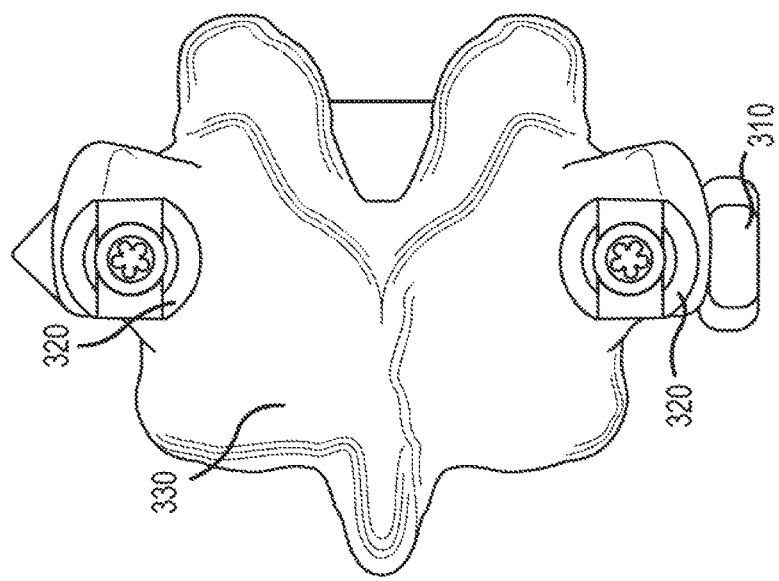
Figure 3H:
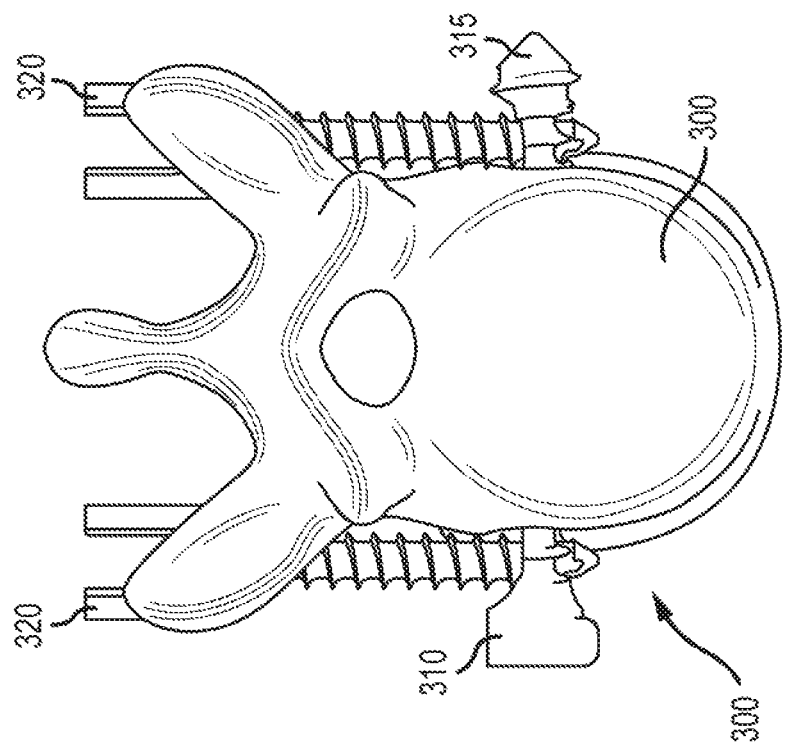
Figure 3G:
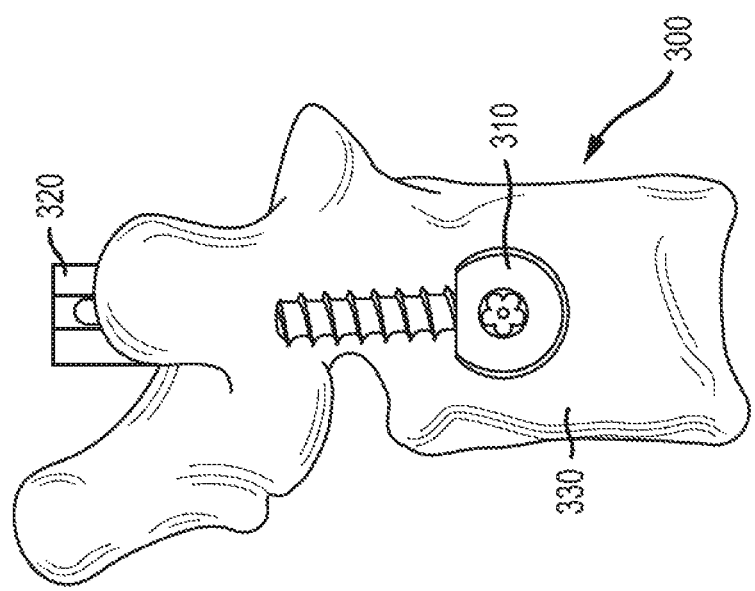

Similarities between system 300 and system 200 include the engagement bar 310 having a lower profile intermediate section 340 and the engagement of the fastener 320 with the engagement bar 310 partially or fully outside of the vertebral body. As shown in FIG. 3D, the height H' of the lower profile intermediate section 340 is smaller than the H' of the lower profile intermediate section 240 shown in, for example 2D. This demonstrates the various differences between height H and height H' that can be used in various embodiments of the engagement bar described herein. Despite these similarities as shown in the Figures, it should be appreciated that system 300 may also be provided without a lower profile intermediate section and/or with fastener/engagement bar engagement outside the vertebral body.

With reference now to FIGS. 4A-4M, a system 400 that uses a locking bar 450 (see Figure, for example, 4E) to secure a fastener 420 (see, for example, FIGS. 4H-4M) to an engagement bar 410 is illustrated. As shown in, for example, FIG. 4E, the engagement bar 410 includes an elongated passage 460 extending through a length of the engagement bar 410 and aligned generally in parallel with a longitudinal axis of the engagement bar 410. The elongated passage 460 as shown in this embodiments extends from a first side of the engagement bar 410 to at least each engagement hole 411. An elongated locking bar 450 is shaped and dimensioned to slide into the passage 460, and can generally be moved in and out of the passage 450 in a direction parallel to the longitudinal axis of the engagement bar 410.

The elongated locking bar 450 further includes one or more locking holes 451. The locking holes 451 are similar to the engagement holes 411 in that they are typically spaced apart a distance and are aligned such that the central axis of the locking holes 411 are aligned in parallel with one another to help ensure that the top openings of each locking hole 451 are on the same face of locking bar 450 and the bottom openings of each locking hole 451 are on the same face of the locking bar 450 (which will generally be opposite the face of the top openings of locking holes 451). The locking holes 451 are also typically spaced apart a distance roughly identical to the distance the engagement holes 411 are spaced apart. In this manner, the locking bar 450 can be positioned within the passage 460 such that the central axes of the locking holes 451 align with the central axes of the engagement holes 411 (for example, as shown in FIG. 4F). In this configuration, a fastener 420 may be passed through the engagement hole 411 and the locking hole 451.

Figure 4B:
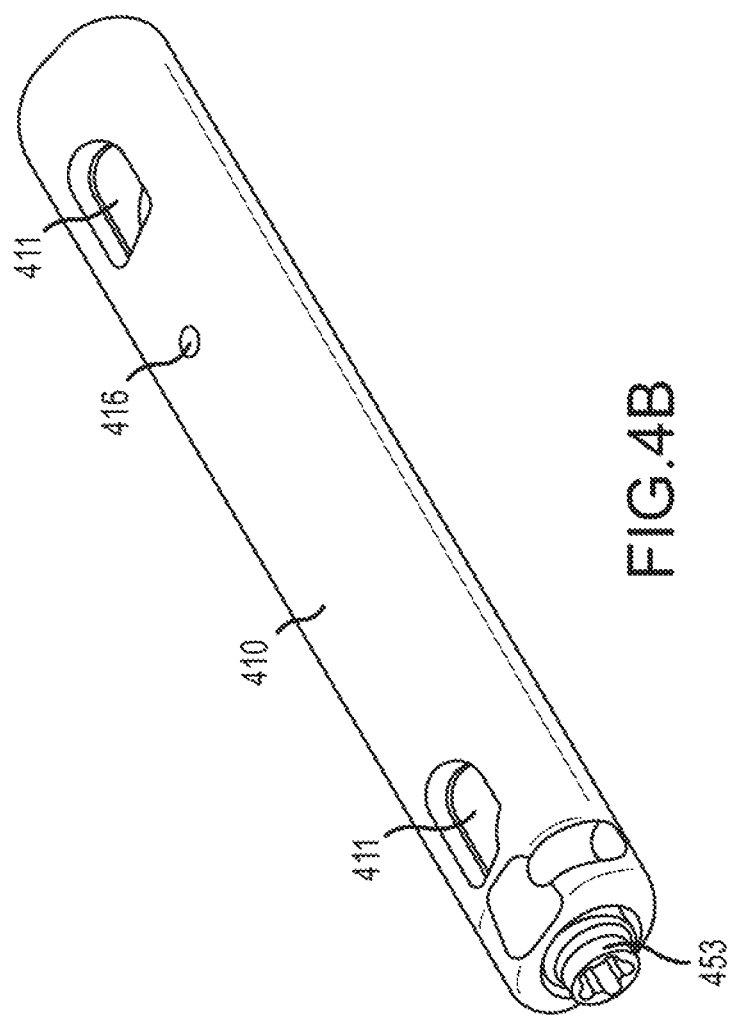
Figure 4A:
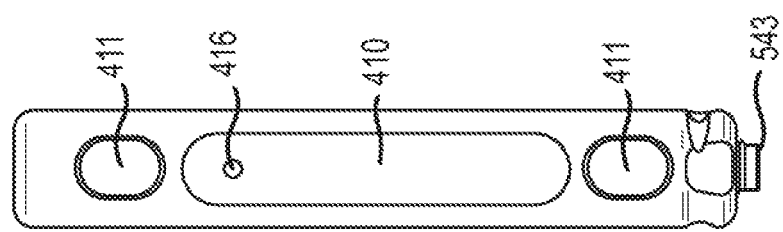
Figure 4E:
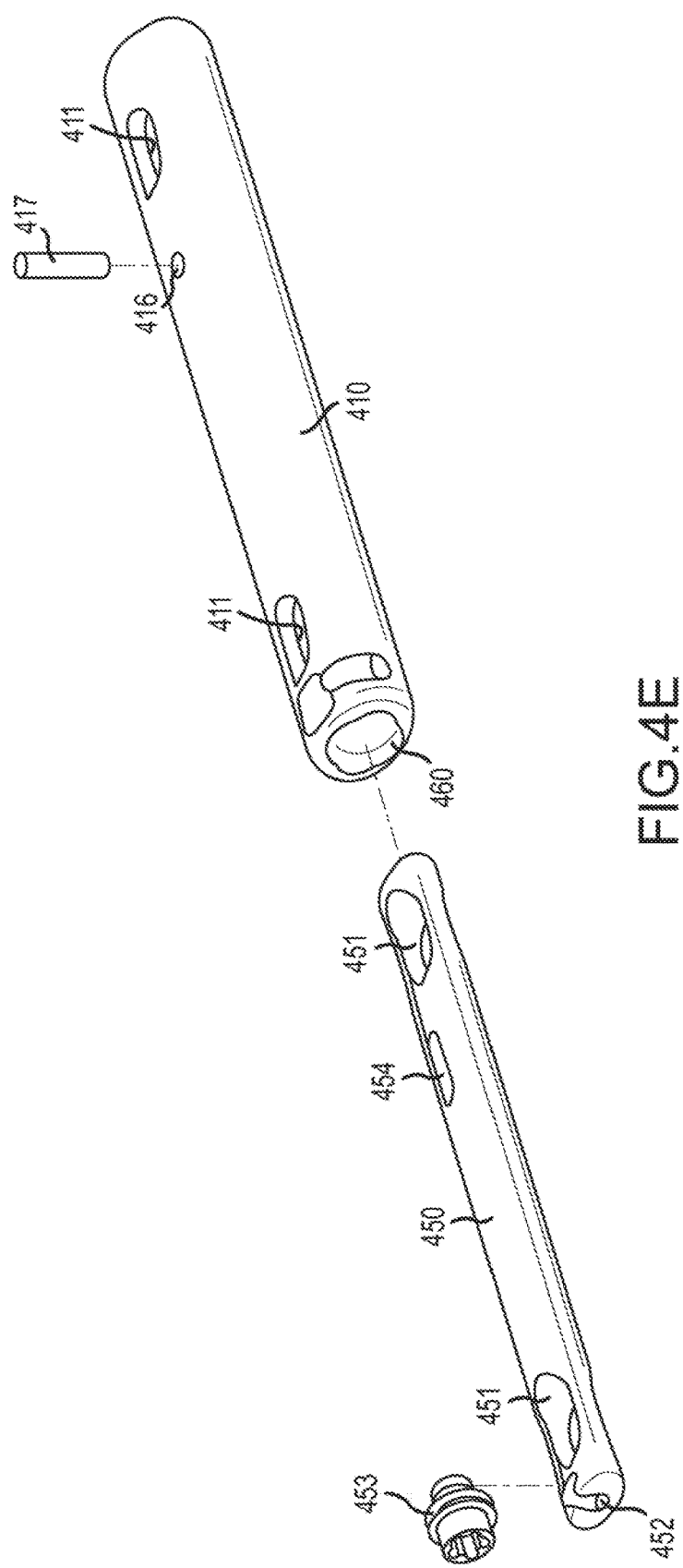
Figure 4I:
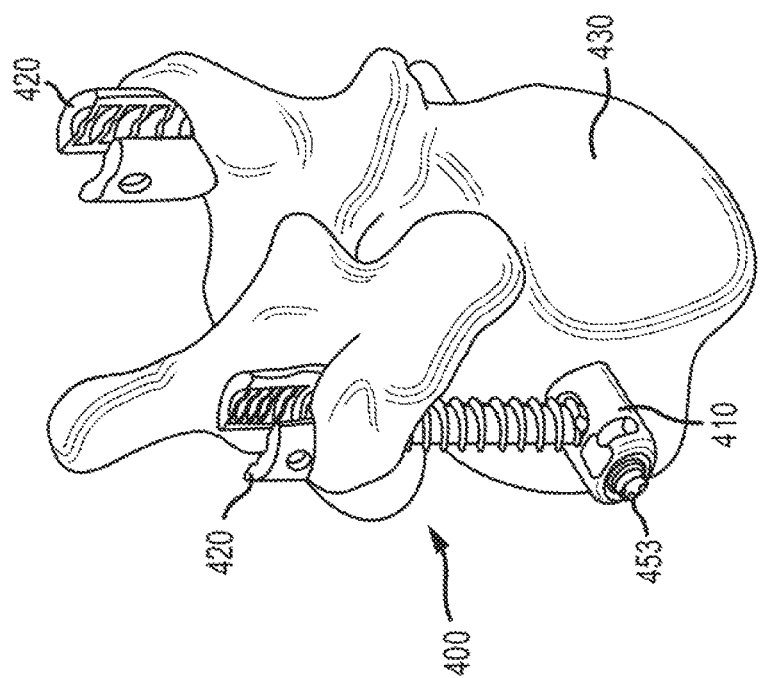
Figure 4H:
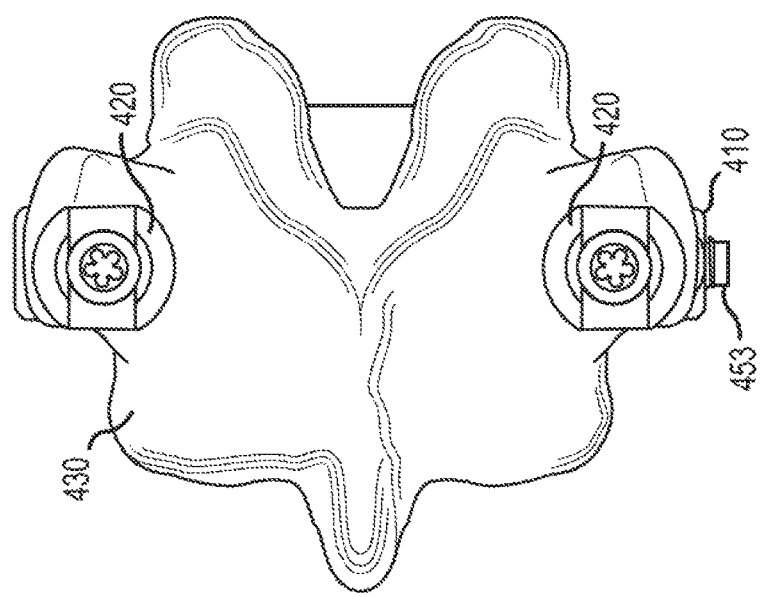
Figure 4M:
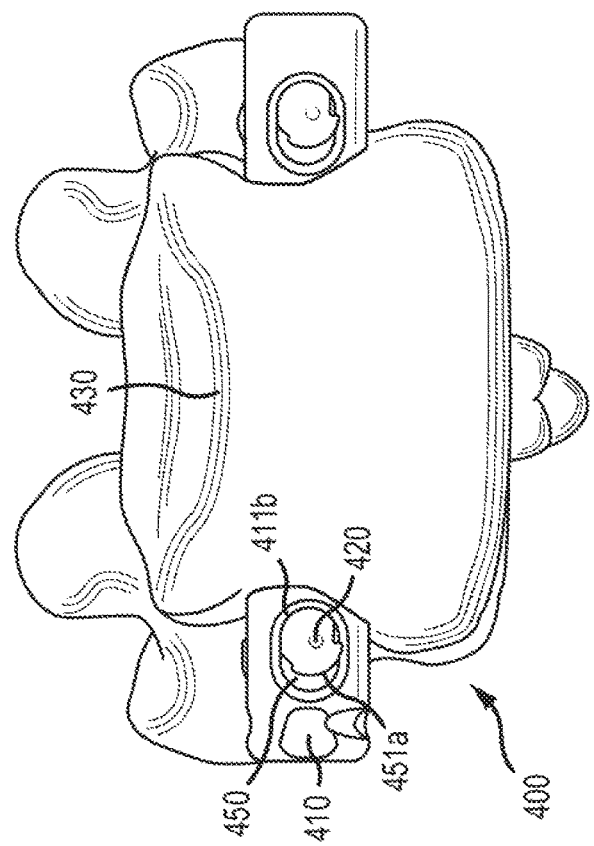
Figure 4L:
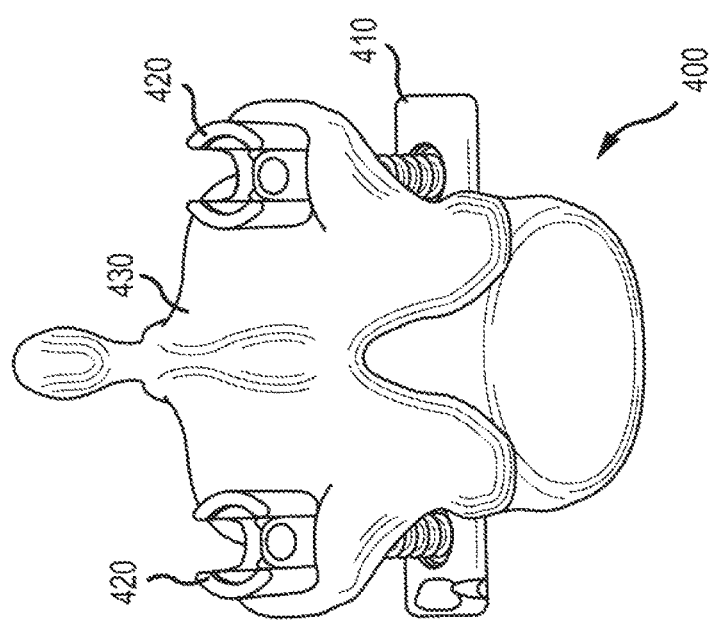
Figure 5D:
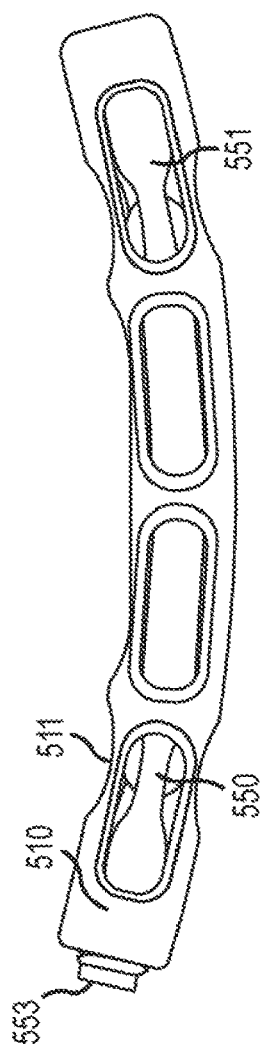
Figure 5C:
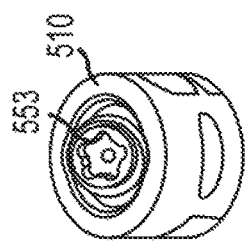
Figure 5E:
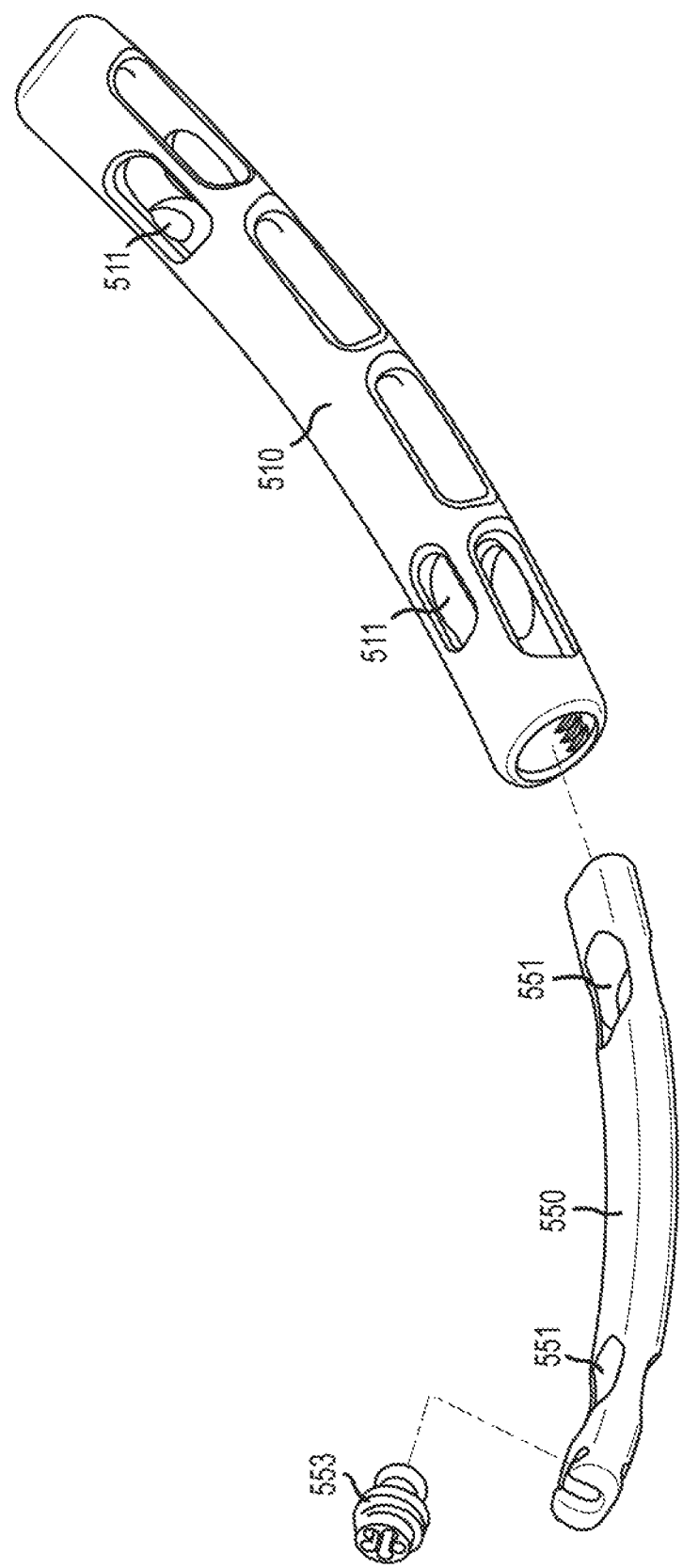
Figure 5I:
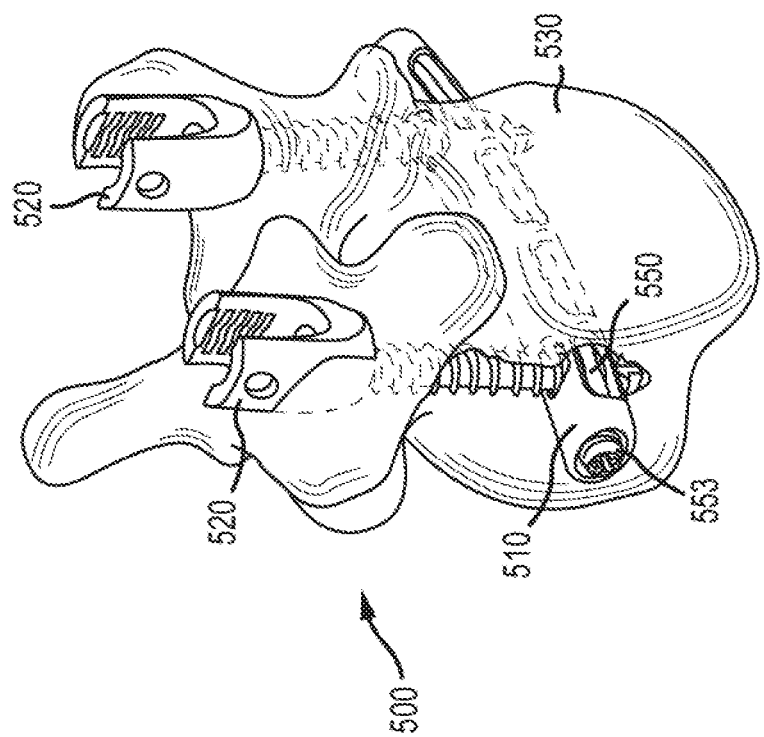
Figure 5H:
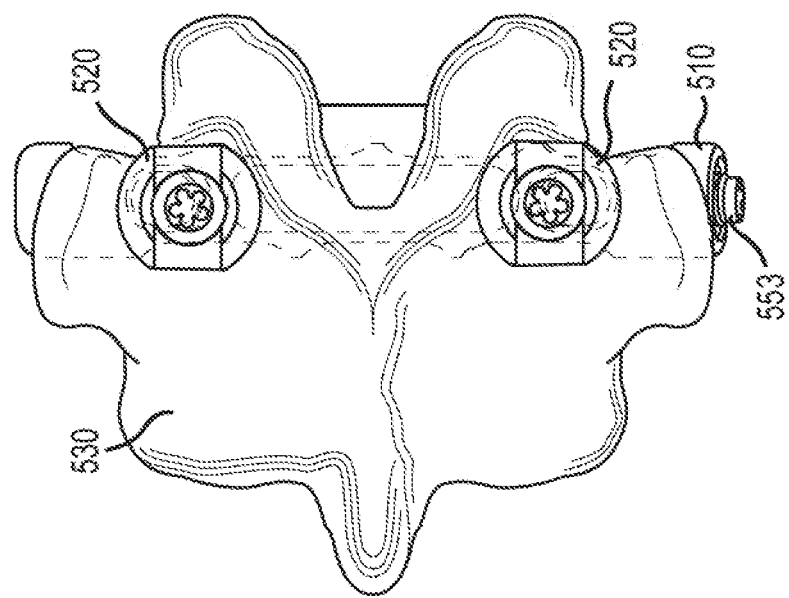
Figure 5K:
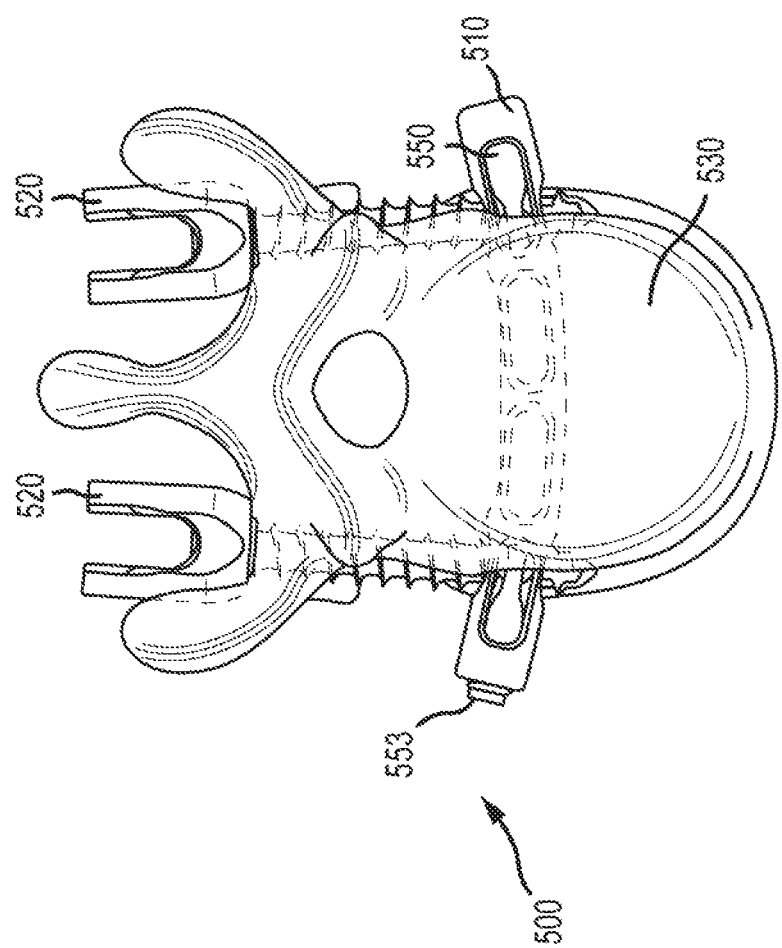
Figure 5J:
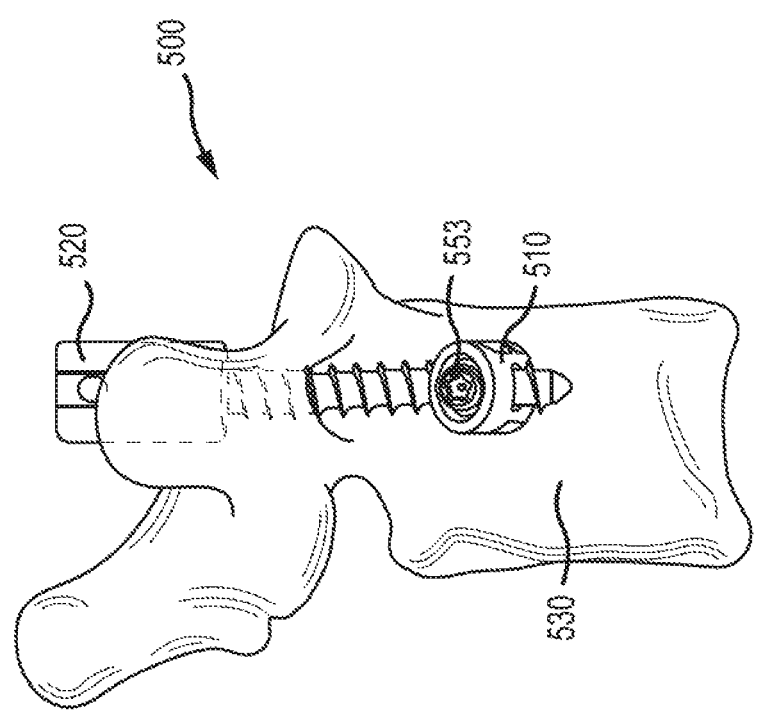
Figure 6B:
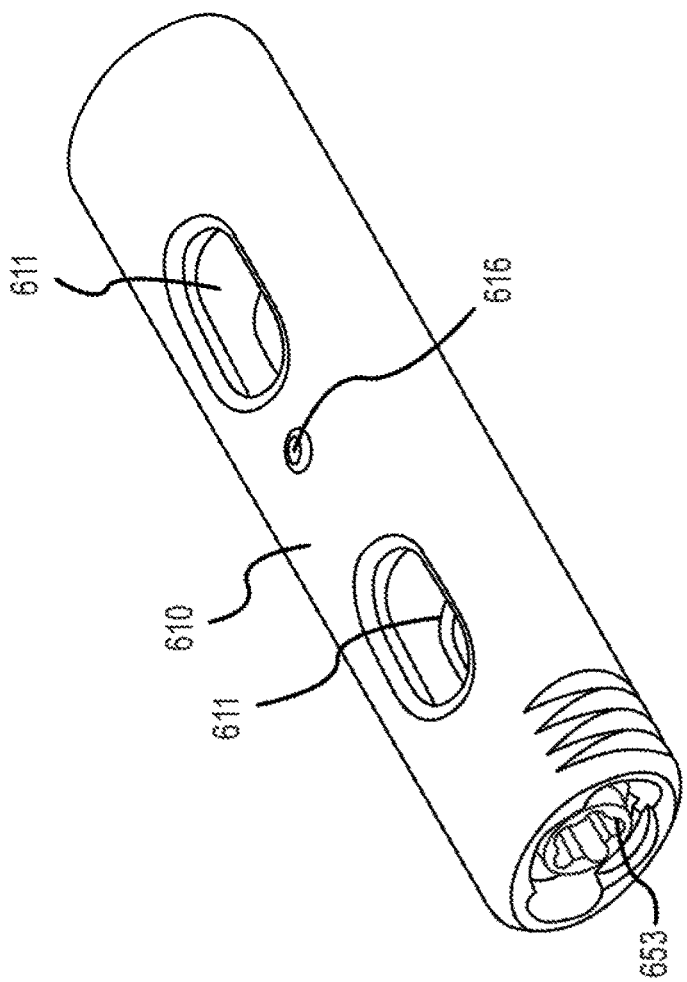
FIGS. 6A-6M illustrate various views of a circumferential vertebral column fixation system in accordance with various embodiments described herein, including views of the circumferential vertebral column fixation system implanted in a vertebra.
Figure 6A:
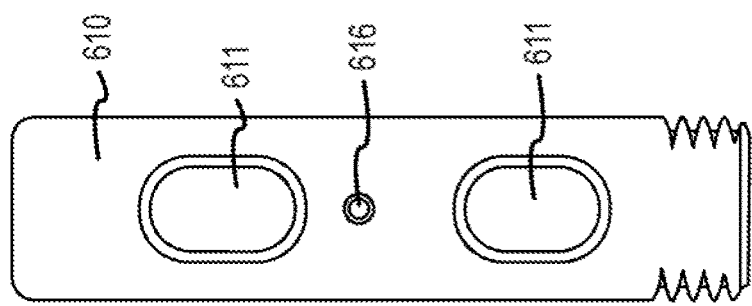
Figure 6D:
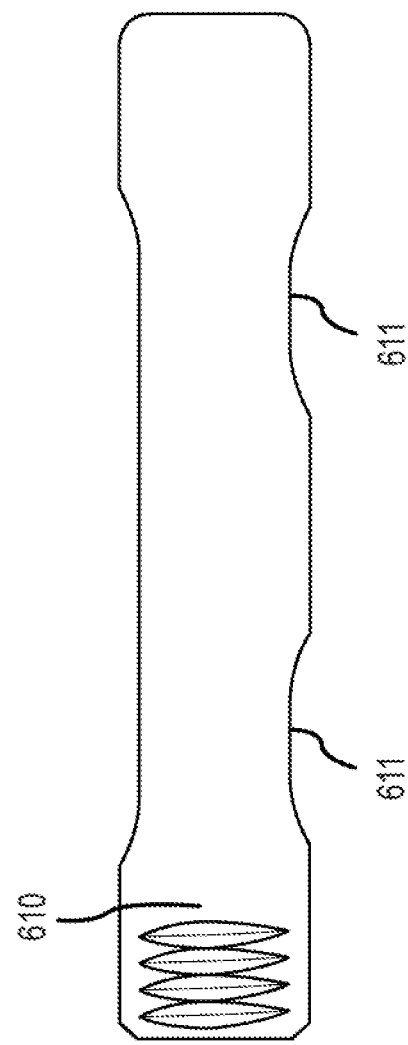
Figure 6C:
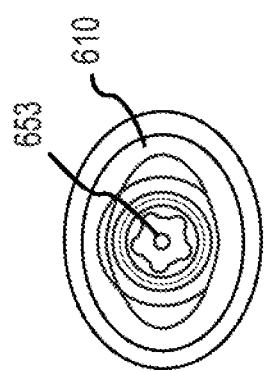
Figure 6E:
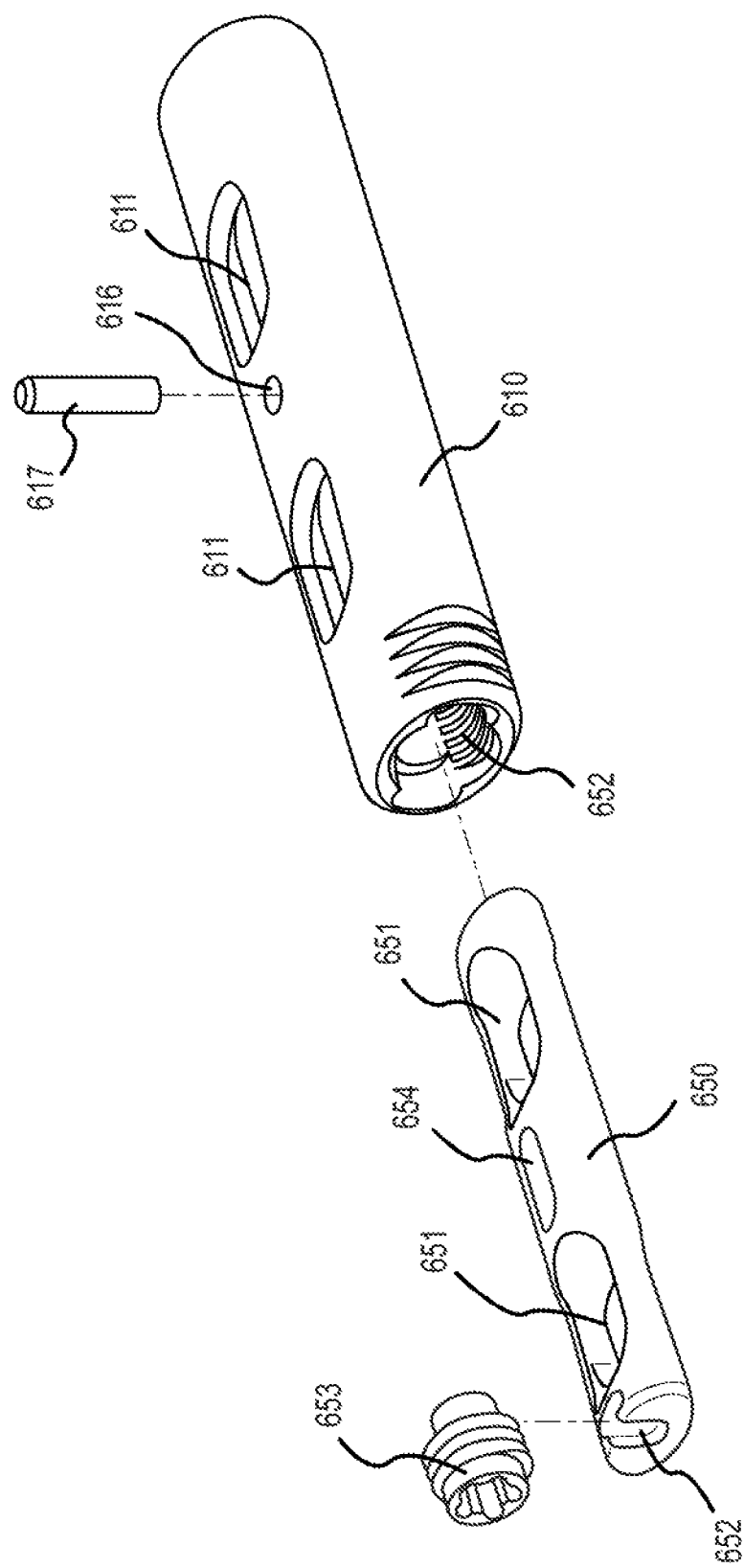
Figure 6G:
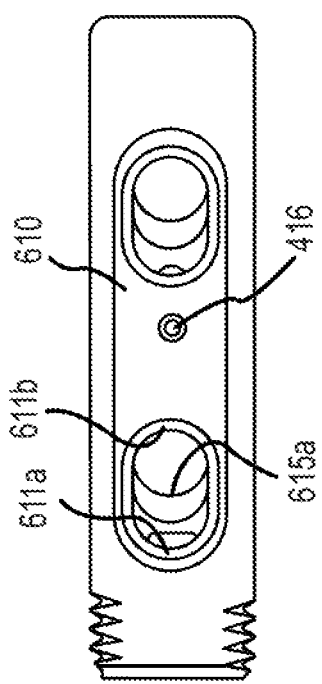
Figure 6F:
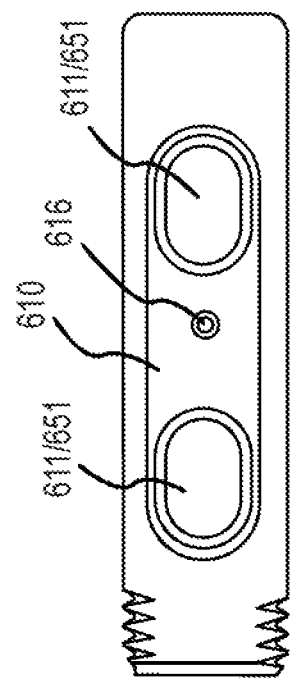
Figure 6I:
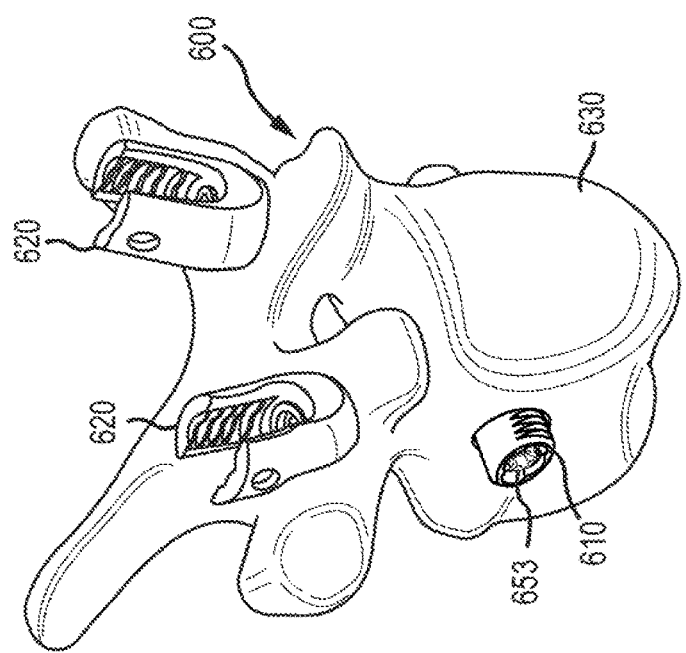
Figure 6H:
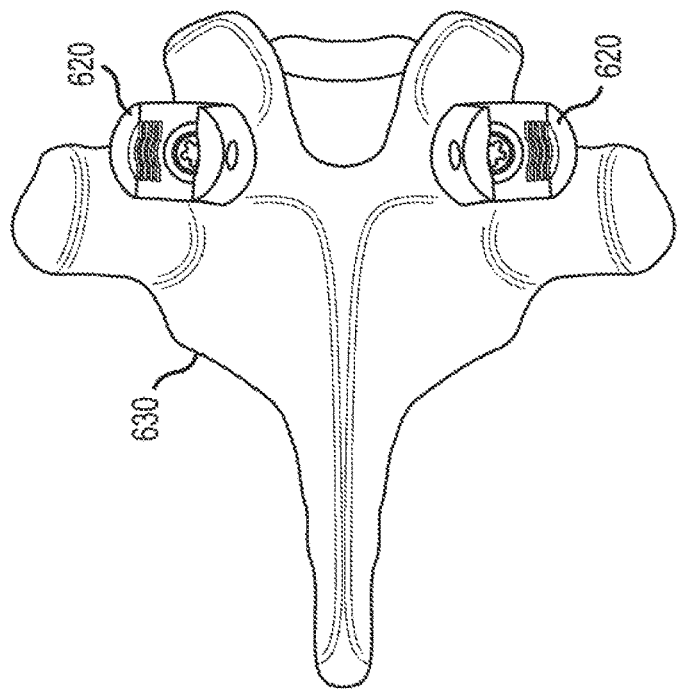
Figure 6K:
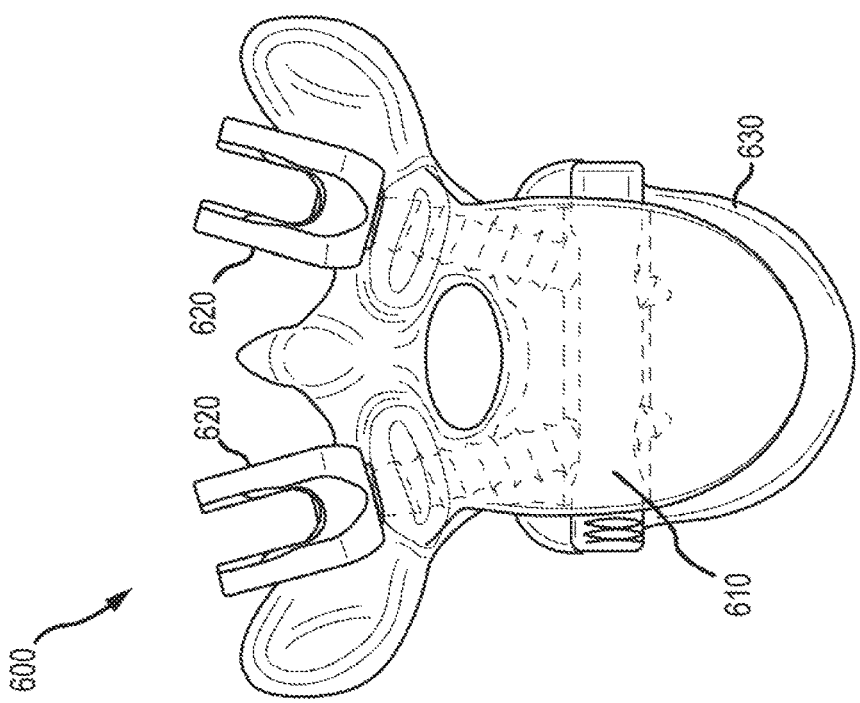
Figure 6J:
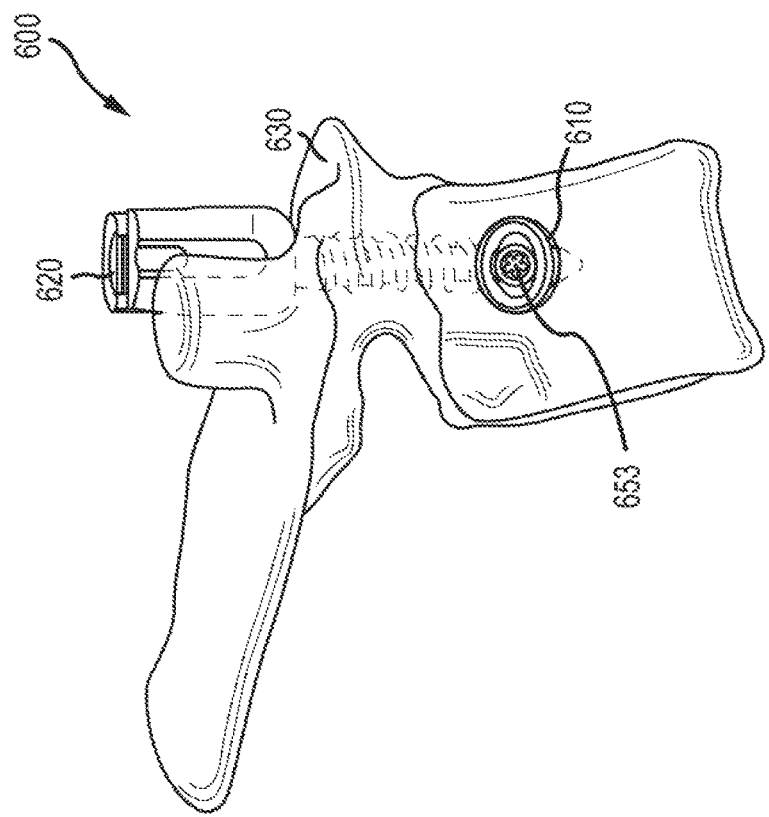
Figure 6M:
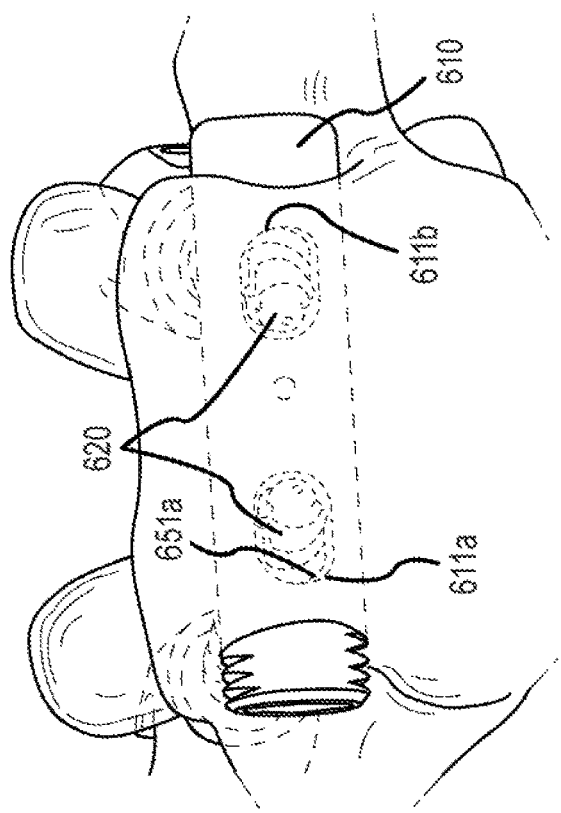
Figure 6L:
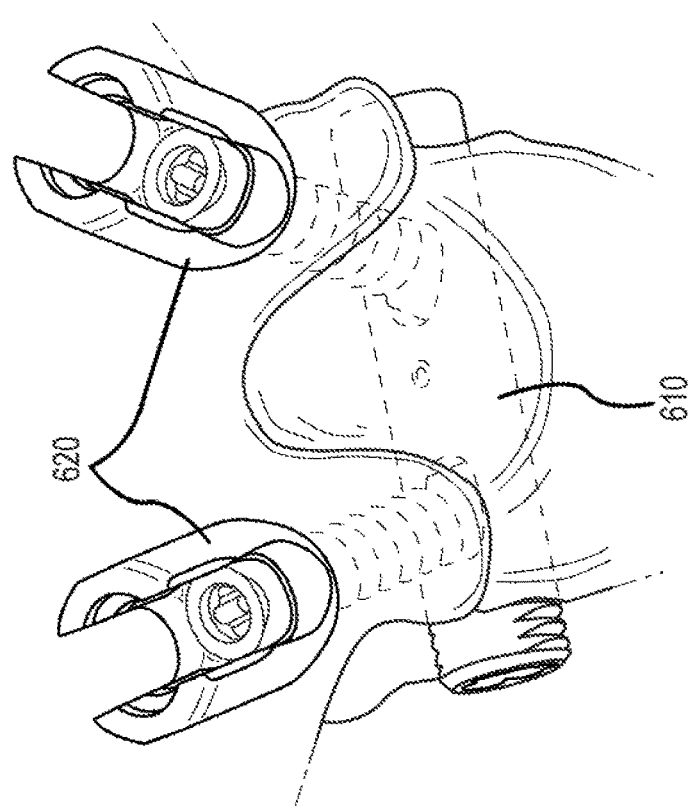
Figure 7B:
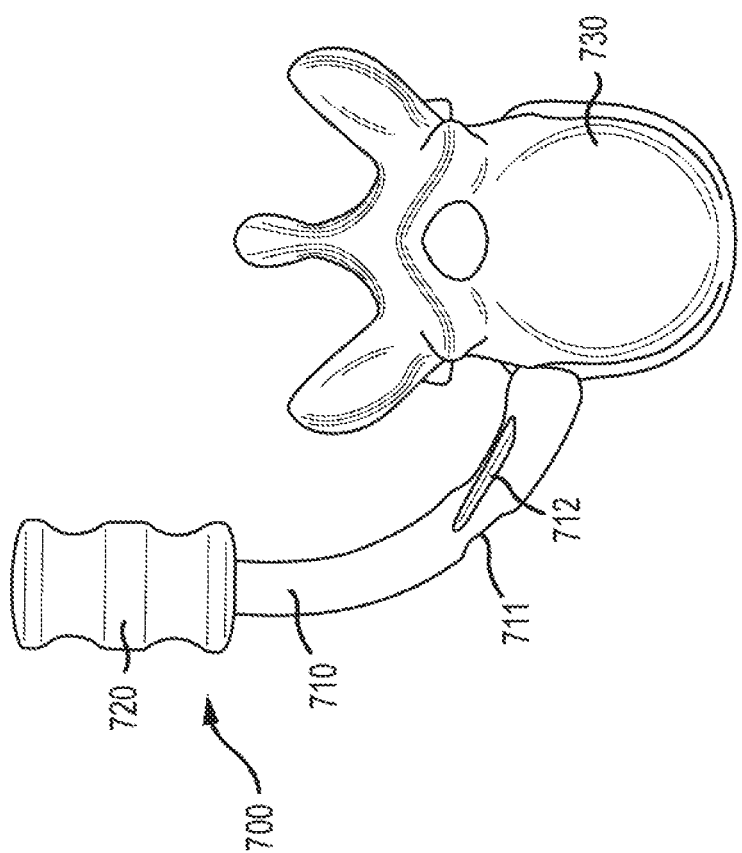
FIGS. 7A-7D illustrate various views of an insertion tool suitable for use with a circumferential vertebral column fixation system according to various embodiments described herein.
Figure 7A:
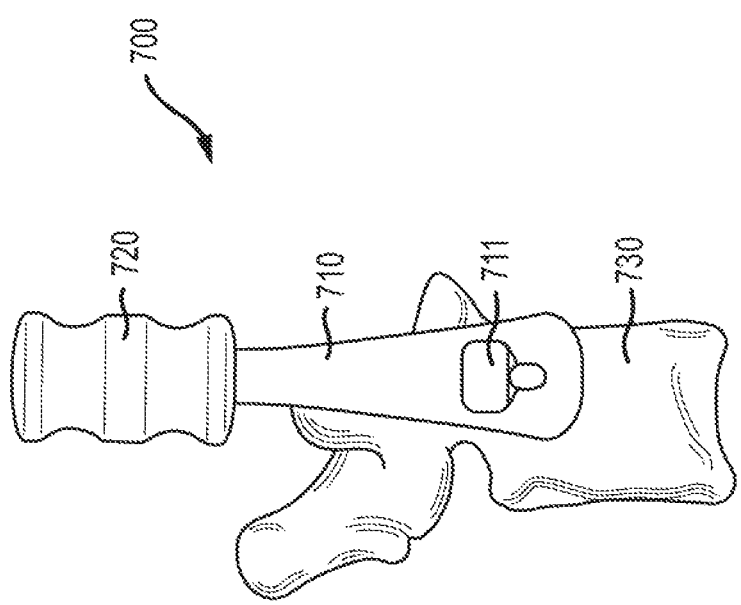
Figure 7D:
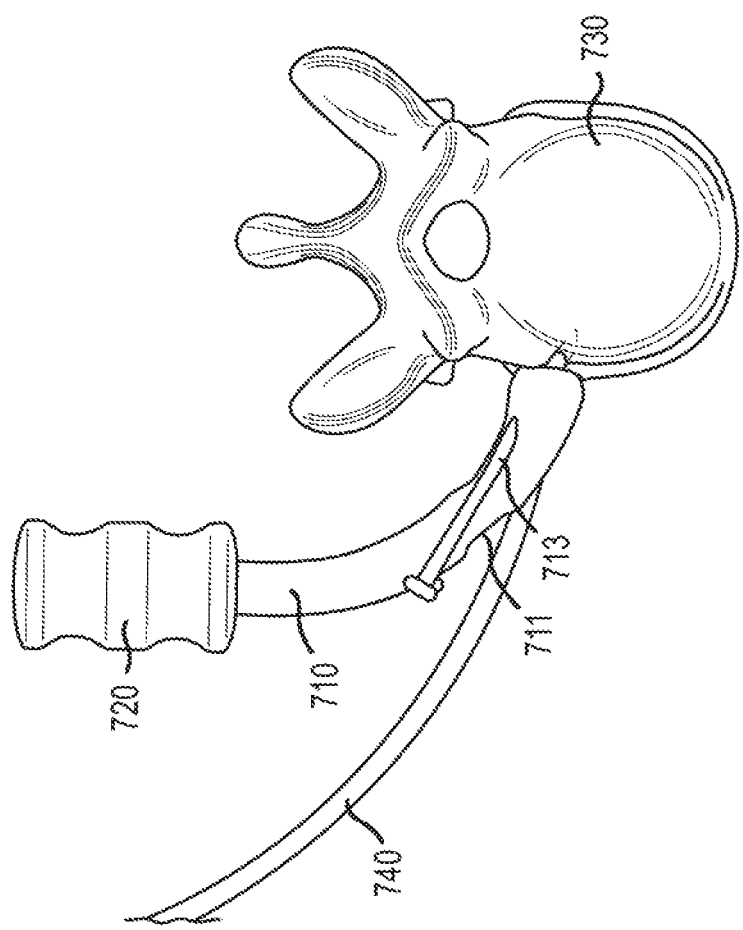
Figure 7C:
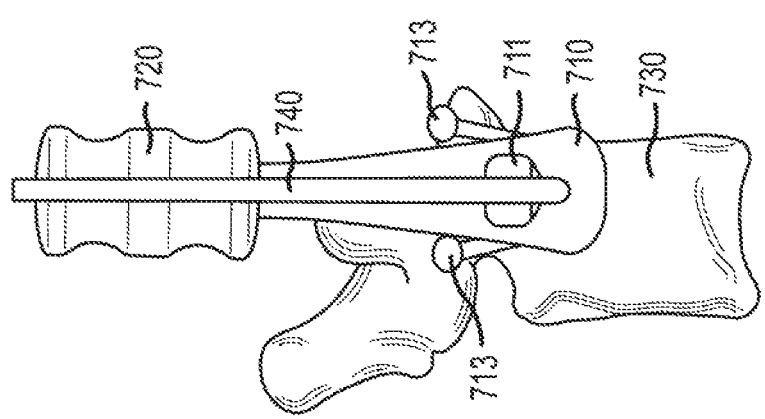

The locking bar 450, the passage 460, and the locking holes 451 also are dimensioned and/or positioned such that a trailing edge 451a of each locking hole can be positioned at least between the trailing edge 411a and leading edge 411b of the engagement holes 411 (for example, as shown in FIG. 4G). This configuration allows for locking a fastener 420 in the engagement hole 411 and the locking hole 451 due to the trailing edge 451a of the locking hole pushing the fastener 420 against the leading edge 411b of the engagement hold 411. Locking the fastener 420 in place typically takes place by sliding the locking bar 450 towards the distal end of the engagement bar 410, as described in one exemplary embodiment below. Notice, the fastener could also be locked in place in a similar fashion by pulling the locking bar towards the proximal end of the engagement bar 410. FIG. 4M, for example, shows the system 400 implanted in a vertebra 430 and further illustrates how the fastener 420 is pushed against the leading edge 411b of the engagement hole by the trailing edge 451a of the locking hole 451 to thereby secure the fastener 420 within the engagement hole 411.

In some embodiments, the locking bar 450 includes a recess 452 (shown in FIG. 4E) into which a locking bar set screw 453 can be placed. The recess 452 is located at one end of the locking bar 450 and can generally be shaped such that the locking bar set screw 453 can freely rotate when placed in the recess 452. The locking bar set screw 453 can include threading on its outer circumference, with the threading designed to engage with threading located at the proximal end of the passage 460. When the locking bar 450 is positioned within the passage 460 such that the locking bar set screw 453 engaged with threading at the proximal end of the passage 460, controlled movement of the locking bar 450 into and out of the passage can be accomplished by rotating the locking bar set screw 453. For example, rotating the locking bar set screw 453 in a clockwise direction causes the locking bar set screw 453 to rotate within the recess 452 while pushing the locking bar 450 forward into the passage 460 by virtue of engagement between the threading on the locking bar set screw 453 and the threading at the proximal end of the passage 460. In some embodiments, the proximal end of the locking bar set screw 453 includes shaped recess into which a tool can engage in order to rotate the locking bar set screw 453. For example, the locking bar set screw 453 can include a hexagonally shaped recess into which an Allen wrench can be placed in order to engage the recess and allow for rotation of the locking bar set screw 453.

In some embodiments, the locking bar set screw 453 is used to carry out the locking of a fastener within the engagement hole 411. The locking bar 450, locking bar set screw 453, and the locking holes 451 can all be appropriately spaced such that the locking holes 451 are aligned with the engagement holes 411 when the threading on the locking bar set screw 453 first engages with the threading at the proximal end of the passage 460. As the locking bar set screw 453 is rotated, the locking bar is forced forward into the passage, which results in the edge 451a of the locking hole 451 moving into the middle of the engagement hole 411 and ultimately pushing the fastener disposed in the engagement hole 411 against the leading edge 411b of the engagement hole 411.

The locking bar 450 and the engagement bar 410 can also include a mechanism designed to keep the locking bar from sliding too far into or too far out of the passage 460. As shown in FIG. 4E, the locking bar 450 can include a set pin slot 454 located between the two locking holes 451 and extending in a direction parallel to the longitudinal axis of the locking bar 450. The engagement bar 411 can include a set pin 416 located between the engagement holes 411. When the locking bar 450 is disposed within the engagement bar, the set pin hole 416 aligns with the set pin slot 454 such that a set pin 417 may be placed in the set pin hole 416 and extend through the set pin slot 454. Once positioned within the set pin hole 416, the set pin 417 allows the locking bar 450 to move back and forth within the passage a distance equal to the length of the set pin slot 454, but prevents any further movement into or out of the passage 460.

With reference to FIGS. 5A-5M, another embodiment of system 500 including an engagement bar 510 and a locking bar 550 is illustrated. Notice, the engagement bar 510 can be used without the locking bar 550 in a manner similar to embodiments of systems described above that do not include a locking bar. In system 500, the engagement bar 510 and the locking 550 are curved, which can aid in the placement of the system 500 within a vertebra 530. The locking bar 550 works in generally the same manner as described above with respect to system 400, including a locking bar set screw 553 that can be used to move the locking holes 551 to a position that is not concentric with the engagement holes 511. More specifically, the rotating the locking bar set screw 553 allows the edge 551a of the locking hole 551 to be positioned between the leading edge 511b and edge 511a of the engagement hole 511.

FIGS. 5A-5M further illustrate a feature which can be included in any of the engagement bars disclosed herein. Specifically, the engagement bar 510 shown in FIGS. 5A-5M illustrate side holes 570 which may be included for a variety of different reasons, including to allow for various biological material that promotes bone growth to be placed around and within the engagement bar. Any number of side holes 570 can be provided along the length of the engagement bar 510, and such side holes 570 are generally oriented so as to have a central axis that is perpendicular to the central axis of the engagement holes 511. As shown in, for example FIG. 5A, the side holes 570 positioned on either side of the engagement bar 510 need not be aligned with one another.

With reference to FIGS. 6A-6M, a system 600 similar to the system 400 shown in FIGS. 4A-4M is shown. One different between the system 400 and the system 600 shown in FIGS. 6A-6M is that the engagement bar 610 and the locking bar 650 have a shorter length than the engagement bar 410 and the locking bar 450 shown in FIGS. 4A-4M. The engagement bar 610 and locking bar 650 may also be wider/thicker than the system 400. This shorter, thicker system 600 may be useful for implantations where it is desired to have the fastener 620 engage with the engagement bar 610 at a location within the vertebra 630. In other words, the engagement bars of earlier embodiments generally had a distance D as shown greater than the medial/lateral width of the vertebral body. However, the embodiment shown in FIGS. 6A-6M has a distance D less than the medial lateral width of the vertebral body.

As with, for example, system 400, the system 600 includes an engagement bar 610 having engagement holes 611, and a locking bar 650 that includes locking holes 651. Each engagement hole includes a leading edge 611b and a trailing edge 611a, and each locking hole 651 includes a trailing edge 651a. The locking bar 650 can move in and out of a passage 660 formed in the engagement bar 610. The engagement bar 611 can further include a set pin hole 616 and a set pin 617. The locking bar 650 can include a recess 652, a locking bar set screw 653 that fits within the recess 652, and a set pin slot 654.

An additional feature of the engagement bar 610 shown in FIGS. 6A-6M (and which can optionally be included in other embodiments disclosed herein) is threading 618 on the outer surface of the engagement bar 610 at a proximal end of the engagement bar 610. The threading 618 can be provided so that a insertion tool can engage with the engagement bar 610 and subsequently be used to implant and position the engagement bar within a vertebra. Such an insertion tool is described below.

The materials used to construct the different elements of the systems described herein (e.g., engagement bar, locking bar, fasteners, etc.) may generally be any materials suitable for use in surgically implanted devices. In some embodiments, the materials are generally biocompatible. Exemplary materials suitable for use in the engagement bar and the locking bar include, but are not limited to, titanium, stainless steel, carbon fiber, Nitinol, cobalt chromium, resorbable material, and PEEK.

The systems described above and illustrated in FIGS. 1A-6M generally include two engagement holes (and two corresponding locking holes when a locking bar is part of the system). As noted previously, the systems described herein may include more than two holes. It should also be noted that the system described herein can include a single hole configuration. Single hole configurations (i.e., where the engagement bar and locking bar (if applicable) each include a single hole) are useful in a variety of situations.

FIGS. 7A-7D illustrate a tool 700 that can be used as part of the process of implanting various embodiments of the circumferential vertebral column fixation system disclosed herein, and specifically the curved system 500 shown in FIGS. 5A-5M. The tool 700 generally includes an elongated curved stem 710 having a handle 720 positioned at a proximal end. Approximately half way down the stem 710, a hollow passage 711 is provided which extends from an external surface of an intermediate portion on the stem 710 to the distal end of the stem 710. The proximal opening of the hollow passage 711 is generally positioned on a lower side of the stem 710. The stem can also include two pin passages 712 positioned in an area similar to the hollow passage 711. The pin passages 712 are generally located on either side of the hollow passage 711 and include an open pin recess portion before transitioning into a passage that extends through the stem 710 and terminates at the distal end of the stem 710. As shown in, for example, FIGS. 7C and 7D, the pin passages 712 receive pins 713 and allow for the distal end of the stem 710 to be secured in place to the vertebra 730. The stem 710 may be hollow from the handle 720 to the distal end of the stem 710 to allow for a flexible drill to be extended to the vertebra. Once secured to the vertebra 730, a guide wire 740 is provided that terminates just under the passage 711. The guide wire 730 can be used for a variety of purposes, such as to guide a drill being used to create a passage within the vertebra and/or to guide an engagement bar or locking bar into the formed passage.

Figure 8A:
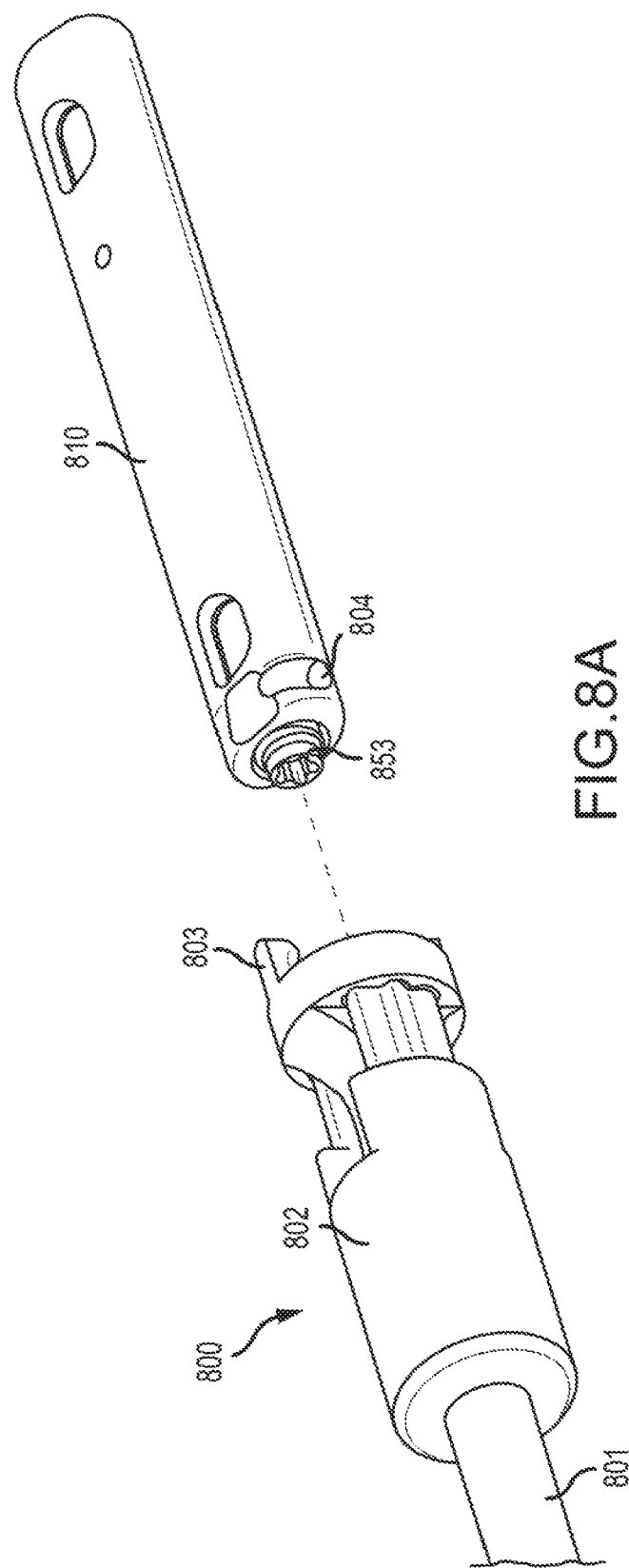
FIGS. 8A-8D illustrate various views of an insertion tool suitable for use with a circumferential vertebral column fixation system according to various embodiments described herein.
Figure 8C:
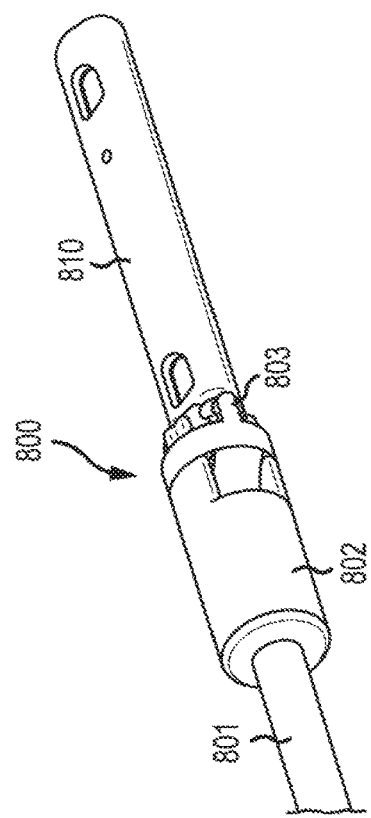
Figure 8B:
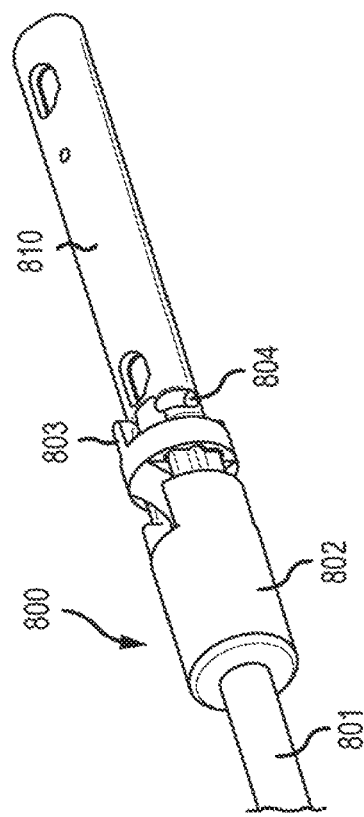
Figure 8D:
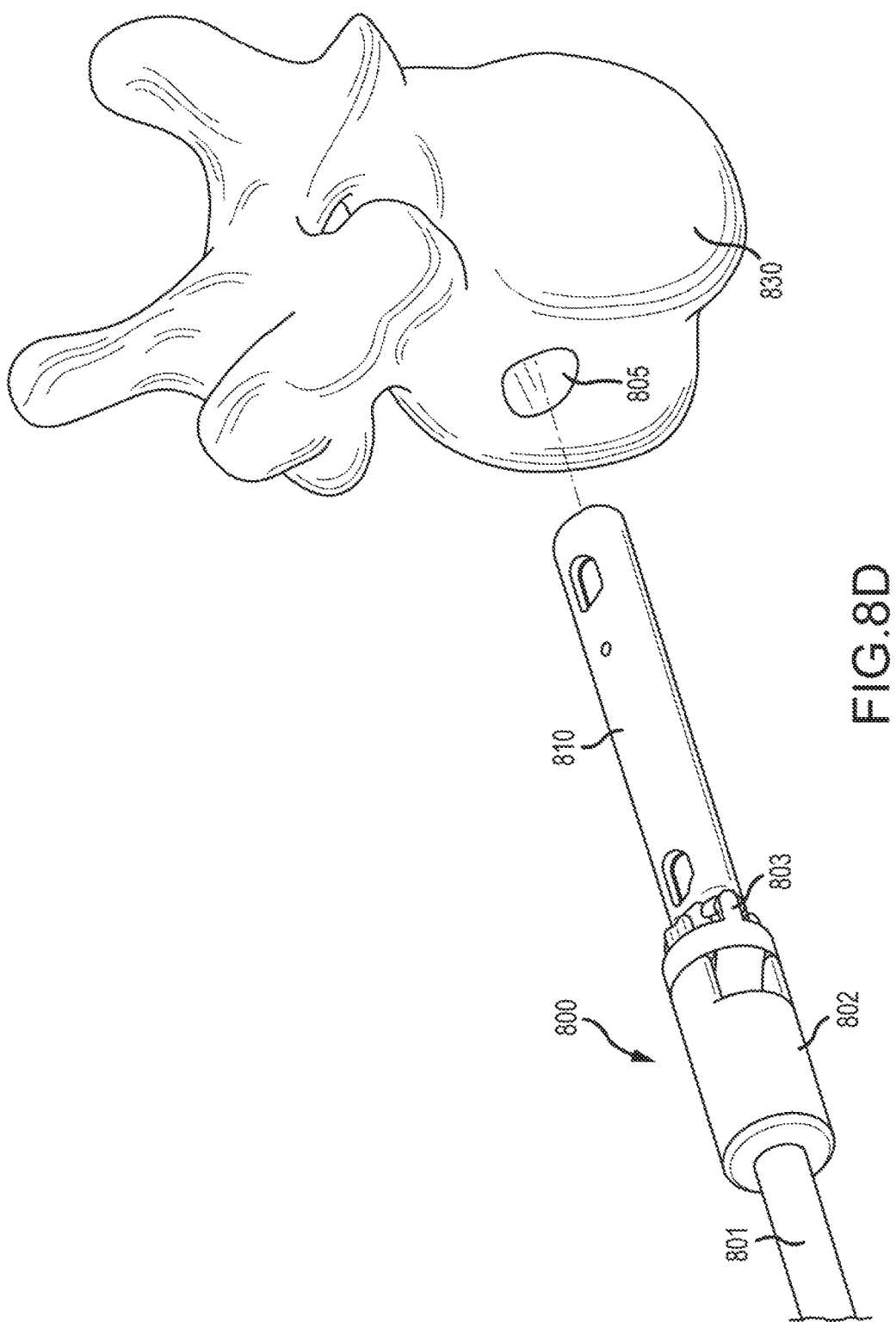

With reference to FIGS. 8A-8D, an embodiment of an insertion tool 800 is shown. The insertion tool includes an elongated stem portion 801 with an engagement tool 802 positioned at the distal end of the stem portion 801. The distal end of the engagement tool 802 includes a tab 803 configured for engaging with a recess 804 located on the proximal end of an engagement bar 810. As shown in, for example, FIGS. 8B and 8C, the distal end of the engagement tool 802 is brought together with the proximal end of the engagement bar. The engagement tool 802 is then rotated, for example, 90 degrees, so that the tab 803 engages the recess 804. In the exemplary embodiments shown, a bulbous end of the tab 803 engages the recess 804 in a type of tongue and groove arrangement. Rotating the engagement tool 802 in this manner engages the tab 803 with the recess and thereby couples the insertion tool 800 with the engagement bar 810. As shown in FIG. 8D, the insertion tool 800 can then be used to guide the engagement bar 810 into a passage 805 formed in a vertebra 830. Once positioned in the passage 805, the insertion tool 800 can also be used to rotate the engagement bar 810 into the desired position. Once the engagement bar is positioned as desired by the surgeon, the engagement tool 802 can be disengaged from the engagement bar 810, such as by rotating the engagement tool 802 in a counter-clockwise direction such that the tab 803 slides out of the recess 804.

The insertion tool 800 shown in FIGS. 8A-8D can also include a mechanism for engaging with locking bar set screw 853. While not shown in FIGS. 8A-8D, the engagement tool 802 can include a male engagement portion located centrally at the distal end of the engagement tool 802. The male engagement portion may be shaped to engage with the female recess at the proximal end of the locking bar set screw 853. When the engagement tool 802 is coupled with the engagement bar 810, the male engagement portion may be rotated independently of the engagement tool 802 so that the engagement tool 802 can stay coupled with the engagement bar 810 while still allowing the locking bar set screw 853 to be moved into or out of the engagement bar 810. For example, in some embodiments, rotating the stem portion 810 results in the rotation of the male engagement portion but does not cause rotation of the engagement tool 802.

FIGS. 9A-9E illustrate yet another insertion tool 900 suitable for use with various circumferential vertebral fixation systems disclosed herein, and specifically, the system shown in FIGS. 6A-6E. The insertion tool 900 is similar to the insertion tool 800 discussed previously, but with a different engagement mechanism between the insertion tool 900 and the engagement bar 910. As shown in FIGS. 9A-9E, the engagement bar 910 includes threading 909 on the exterior surface of the proximal end. The engagement tool 902 positioned at the distal end of the stem portion 901 of the insertion tool 900 includes threading configured to mate with the threading 909 of the engagement bar 910. In some embodiments, this threading is located on an interior surface at the distal end of the outer portion 902a of the engagement tool 902. Once the threading 909 of the engagement bar 910 is engaged with the threading on the insertion tool 900, the engagement bar 910 is coupled with the insertion tool 900 can the insertion tool can be used to implant the engagement bar 902 into a passage 905 in a vertebra 930.

The insertion tool 900 also includes tabs 903 that engage with the locking bar set screw 953. These tabs 903 can be part of an interior portion 902b of the engagement tool 902. The tabs 903 are configured to engage with the locking bar set screw 953 so that the rotation of the interior portion 902b and tabs 903 causes the locking bar set screw 953 to rotated and move the locking bar into our out of the engagement bar 910. In some embodiments, the interior portion 902b and tabs 903 are capable of being rotated independently of the outer portion 902b of the engagement tool so that the locking bar set screw 953 can be rotated without decoupling the engagement tool 902 from the engagement bar 910. As shown in FIGS. 9C and 9D, the insertion tool 900 can work by first engaging the tabs 903 with the locking bar set screw 953 and then rotating the outer portion 902a forward and over the inner portion 902b and tabs 903 to engage with the threading 909 on the engagement bar 910.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:
1. A circumferential vertebral column fixation system comprising:
   an elongated engagement bar configured to traverse through a spinal bony segment, the elongated engagement bar comprising:
      a first terminal end and a second terminal end opposite the first terminal end;
      at least two spaced apart fastener holes, each of the fastener holes having a first opening positioned on a top surface of the engagement bar and a second opening positioned on a bottom surface of the engagement bar opposite the top surface; and
      a circumferentially enclosed hollow passage having an opening at the second terminal end of the elongated engagement bar;
   an elongated locking bar configured to fit within the hollow passage and move back and forth along the longitudinal axis of the hollow passage, the locking bar comprising:
      a first terminal end and a second terminal end opposite the first terminal end; and
      at least two spaced apart locking holes, each of the locking holes having a first opening positioned on a top surface of the locking bar and a second opening positioned on a bottom surface of the locking bar opposite the first top surface;
      wherein the at least two locking holes are spaced apart a similar distance to the at least two fastener holes, and wherein the locking bar can be positioned within the hollow passage such that the locking holes align with the fastener holes; and
   at least one fastener configured to engage with each pair of aligned fastener hole and locking hole;
   wherein the first terminal end of the elongated locking bar and the second terminal end of the elongated locking bar are located entirely within the hollow passage when the elongated locking bar engages the at least one fastener to secure the at least one fastener within one of the at least two spaced apart fastener holes.

2. The system of claim 1, wherein the length of the elongated locking bar and the length of the hollow passage are each sized such that the elongated locking bar can be positioned within the hollow passage such that a trailing edge of each locking hole in the elongated locking bar is positioned between a leading edge and a trailing edge of the fastener holes in the elongated engagement bar.

3. The system of claim 1, wherein the hollow passage includes threading proximate the opening at the one end of the elongated engagement bar, and the system further comprises:

a locking bar set screw comprising threading configured to mate with the threading proximate the opening at the one end of the hollow passage, the locking bar set screw configured to rotatingly engage with a trailing end of the locking bar.

4. The system of claim 1, wherein the elongated engagement bar includes a set pin hole between the at least two engagement holes, the set pin hole having an axis generally parallel with the axes of the engagement holes;
   wherein the elongated locking bar includes an elongated slot aligned in parallel with the longitudinal axis of the elongated locking bar; and
   wherein the system further comprises a set pin configured to pass through the set pin hole and the elongated slot.

5. The system of claim 1, wherein the material of the elongated engagement bar and the elongated locking bar is selected from the group consisting of titanium, stainless steel, carbon fiber, Nitinol, cobalt chromium, resorbable material, and PEEK.

6. The system of claim 1, wherein each of the at least two locking holes have a length, a width, and a depth, the length being parallel to the longitudinal axis of locking bar and the width being transverse to the longitudinal axis of the locking bar;
   wherein the length is greater than the diameter of the fastener and the width is approximately equal to the diameter of the fastener.

* * * * *